(12) United States Patent
Jeong et al.

(10) Patent No.: US 9,034,258 B2
(45) Date of Patent: May 19, 2015

(54) MOLECULARLY IMPRINTED POLYMER FOR DETECTING THE PENTRAXIN, AND METHOD FOR PREPARING SAME

(75) Inventors: Sang Won Jeong, Daegu (KR); Eun Joo Kim, Daegu (KR); Hyun-Chul Kim, Daegu (KR); Se Geun Lee, Daegu (KR); Sung Jun Lee, Daegu (KR)

(73) Assignee: DAEGU GYEONGBUK INSTITUTE OF SCIENCE AND TECHNOLOGY, Daegu (KR)

( * ) Notice: Subject to any disclaimer, the term of this patent is extended or adjusted under 35 U.S.C. 154(b) by 759 days.

(21) Appl. No.: 13/297,556

(22) Filed: Nov. 16, 2011

(65) Prior Publication Data
US 2012/0128536 A1  May 24, 2012

Related U.S. Application Data

(63) Continuation-in-part of application No. PCT/KR2010/005059, filed on Jul. 30, 2010.

(30) Foreign Application Priority Data

Dec. 29, 2009 (KR) .................. 10-2009-0133048

(51) Int. Cl.
*G01N 15/06* (2006.01)
*G01N 33/531* (2006.01)
*G01N 33/68* (2006.01)

(52) U.S. Cl.
CPC .......... *G01N 33/531* (2013.01); *G01N 33/6893* (2013.01); *G01N 2333/4737* (2013.01); *G01N 2600/00* (2013.01)

(58) Field of Classification Search
USPC ............... 422/50, 68.1; 436/43; 522/181; 526/318.41
See application file for complete search history.

(56) References Cited

U.S. PATENT DOCUMENTS

| 5,310,648 A | 5/1994 | Arnold et al. |
| 2006/0246522 A1 | 11/2006 | Bhullar et al. |
| 2010/0151580 A1* | 6/2010 | Peppas et al. .................. 436/86 |

(Continued)

FOREIGN PATENT DOCUMENTS

| GB | 2217335 A | 10/1989 |
| JP | 2004-018576 A | 1/2004 |

(Continued)

OTHER PUBLICATIONS

Meyer, et al., "SPR-based Immunosensor for the CRP Detections—A New Method to Detect a Well Known Protein" Biosensors & Bioelectronics, pp. 1987-1990, 2006.
Chou, et al., "Fiber Optic Biosensor for the Detection of C-reactive Protein and the Study of Protein Binding Kinetics" J. Biomed Opt., Mar.-Apr. 2007.

(Continued)

*Primary Examiner* — Brian J Sines
(74) *Attorney, Agent, or Firm* — Pearne & Gordon LLP

(57) ABSTRACT

The present disclosure relates to a molecularly imprinted structure for detection of a pentraxin protein and a method for preparing the same by synthesizing a reactive group-pentraxin protein ligand complex specifically reacting with the pentraxin protein and being polymerizable with a crosslink agent to detect a pentraxin protein by using the complex. The present disclosure also provides a chip for detection of a C-reactive protein and a method for preparing the same, the chip including a molecularly imprinted layer having excellent sensitivity to a C-reactive protein and an improved binding force to a metal substrate by using click chemistry.

10 Claims, 17 Drawing Sheets

(56) References Cited

U.S. PATENT DOCUMENTS

2013/0183243 A1* 7/2013 LaBelle et al. ............... 424/9.1
2013/0217598 A1* 8/2013 Ludwig et al. ................ 506/16

FOREIGN PATENT DOCUMENTS

| KR | 10-2004-0064054 A | 7/2004 |
| KR | 10-2008-0081442 A | 9/2008 |
| KR | 10-0861452 B1 | 10/2008 |
| WO | 2005-063382 A1 | 7/2005 |
| WO | 2007-050333 A | 3/2007 |

OTHER PUBLICATIONS

Sui, et al., "Calcium-Dependent Binding of Rabbit C-Reactive Protein to Supported Lipid Monolayers Containing Exposed Phosphorylcholine Group" Biophysical Journal, vol. 76, Jan. 1999, pp. 333-341.
Rosenzweig, et al., "Multivalent Protein Binding and Precipitation by Self-Assembling Molecules on a DNA Pentaplex Scaffold" Department of Chemistry, Yale University, published Feb. 18, 2009.
International Search Report for PCT/KR2010/005059 dated Apr. 29, 2011.

* cited by examiner (a) NaN₃, KI, EtOH  (b) methanesulfonyl chloride, TEA, THF (c) KSCOCH₃, DMF  (d) HCl, MeOH (a) Propargyl bromide, NaH, DMF  (b) COP, TEA, DCM, rt  (c) TMA, ACN, 60°C

MOLECULARLY IMPRINTED POLYMER FOR DETECTING THE PENTRAXIN, AND METHOD FOR PREPARING SAME

CROSS-REFERENCE TO RELATED APPLICATION

This application claims the benefit of International Application No. PCT/KR2010/005059 filed Jul. 30, 2010, which claims Korean Patent Application No. 10-2009-0133048 filed on Dec. 29, 2009, the entire disclosures of which are incorporated herein by reference.

FIELD OF THE INVENTION

The present disclosure relates to a molecularly imprinted structure for detection of a pentraxin protein and a method for preparing the same, more particularly, to a method for preparing a molecularly imprinted polymer for detection of a pentraxin protein, the method including preparing a reactive group-pentraxin protein ligand (L-S—R), in which a reactive group (R) and a pentraxin protein ligand (L) are bound together, reacting the reactive group-pentraxin protein ligand (L-S—R) with a pentraxin protein, and then, mixing the reacting material with a crosslink agent and an initiator, and performing a photo-polymerization or thermal polymerization reaction to prepare a polymer to which a ligand molecularly imprinted with a pentraxin protein is bound.

The present disclosure also relates to a chip for detection of a C-reactive protein and a method for preparing the same, the chip including a molecularly imprinted layer having excellent sensitivity to a C-reactive protein and an improved binding force to a metal substrate by using click chemistry.

BACKGROUND OF THE INVENTION

A pentraxin protein is one of protein groups. The pentraxin protein is involved in calcium-dependent ligand binding and has a plane β-structure. The word "pentraxin" is derived from the Greek words for five (penta) and berries (ragos). The pentraxin protein is formed with five monomers arranged in a regular pentagon shape and has a diameter of about 9.5 nm and a height of about 3.5 nm. A relatively small pentraxin protein includes a serum amyloid P component (SAP) and a C-reactive protein (CRP). A relatively large pentraxin protein includes PTX3 (cytokine regulatory molecule) and other nervous proteins.

The CRP is one of representative acute-phase reactive proteins for tissue damage or inflammation in mammals. The CRP is used as a diagnosis factor for various inflammatory diseases and cardiac infarction. The SAP is a vertebrate protein, which is a precursor of the amyloid component P, and observed in all types of amyloid deposits for glomerular basement membranes and elastic fibers in blood vessels. The SAP is an important molecule marker for the Alzheimer disease and utilized for the disease diagnosis.

With respect to a conventional method for detection of a C-reactive protein, there have been reported a method using an antibody (Korean Patent Application Publication No. 2004-0064054), a method using a phosphocholine ligand (U.S. Pat. No. 0,246,522 and British Patent No. 02217335), and other methods. In case of using the antibody, a high cost for preparing an antibody is required. In order to maintain activity of an antibody, it is necessary to manage whether the activity is deteriorated, using a special storage method. In case of using the phosphocholine ligand, an intermediate to fix the ligand to a protein, agarose gel, polystyrene, or others is needed.

In order to overcome the problems, many researchers have put forth their efforts in developing detection methods using a molecularly imprinted polymer having excellent stability, compared to an antibody. Accordingly, the present disclosure provides a method for preparing a molecularly imprinted polymer to increase an effect of detection of a C-reactive protein, which is a representative example of pentraxin proteins. To the end, the inventors of the present disclosure developed a novel molecularly imprinting technology using a phosphocholine ligand, by synthesizing styrene-phosphocholine ligands including a phosphocholine group designed to be polymerized with styrene that is a crosslink agent, and inducing a polymerization reaction of the crosslink agent in the state that the styrene-phosphocholine ligands are simultaneously bound to five phosphocholine ligand binding sites present in a C-reactive protein.

BRIEF SUMMARY OF THE INVENTION

In view of the foregoing, the present disclosure provides a molecularly imprinted structure for detection of a pentraxin protein and a method for preparing the same by synthesizing a reactive group-pentraxin protein ligand complex specifically reacting with the pentraxin protein and being polymerizable with a crosslink agent to detect a pentraxin protein by using the complex.

The present disclosure also provides a chip for detection of a C-reactive protein and a method for preparing the same, the chip including a molecularly imprinted layer having excellent sensitivity to a C-reactive protein and an improved binding force to a metal substrate by using click chemistry.

In accordance with one aspect of an the present disclosure, there is provided a method for preparing a molecularly imprinted structure for detection of a pentraxin protein, the method including: binding a pentraxin protein and a reactive ligand having a following structural formula; chemically reacting the complex of the pentraxin protein and the reactive ligand on a reactive surface of a support; and removing the pentraxin protein from the reacting material by washing the reacting material with an elution buffer solution.

L-S—R [Structural Formula]

L: Ligand for binding with the pentraxin protein
R: Reactive group
S: Linker for linking between the ligand for binding with the pentraxin protein and a reactive group In an illustrative embodiment, the pentraxin protein is formed with five monomers arranged in a regular pentagon shape and has a diameter of about 9.5 nm and a height of about 3.5 nm. Since each one ligand is bound to each of the monomers of the pentraxin protein, five reactive ligands in the embodiment are bound to one pentraxin protein (see FIG. 1.)

The "reactive ligand" refers to a material where ligand (L) capable of being bound to a pentraxin protein, which is target molecule, to form a complex, and reactive group (R) capable of being bound to a reactive surface of a support through a polymerization or chemical reaction are linked by a linker (S). The intermediate linker (S) intermediates the binding between the ligand (L) and the reactive group (R) and makes the binding to the support flexible. That is, one end of the reactive ligand is formed with a ligand (L) bound to a target material. The other end of the reactive ligand is formed with a reactive group (R) capable of being polymerized or bound to a metal material.

The "support" is a solid polymer or a metallic material that serves as a body of a molecularly imprinted structure, and may be in form of a plate, film, nano-particle, nano-wire, porous particle, or bead. A metallic material support may be prepared separately, while a polymer support may be prepared in situ through a polymerization reaction with reactive ligand having polymerizable reactive group.

The "reactive surface" is a layer separated from an aqueous solution layer in a buffer solution and refers to a surface of an organic material that can be polymerized reaction (e.g., copolymerization) with a reactive group of a reactive ligand or a surface of a metallic material that can be chemically bound to the reactive group. In the embodiment, for the reactive surface of the organic material, a material in which styrene and DVB are mixed with a ratio of 9:1 is used. The mixture is not mixed with an aqueous solution and forms a layer on the surface of the aqueous solution. In this case, the reactive surface refers to an interface between the aqueous solution and the layer of the mixture of styrene/DVB and is copolymerized with a reactive ligand in the aqueous solution. After the copolymerization is finished, the reactive surface is modified by the reactive ligand (see FIG. 5).

The words "molecularly imprinted structure" used in illustrative embodiments mean a imprinted material having a ligand or space capable of binding with target molecule by using target molecular as template. Particularly, the "molecularly imprinted polymer (MIP)" refers to a polymer which is synthesized by using a monomer being bound to a proper template as a starting material, and then the template is removed, so that the polymer has a space in the same shape as that of the template. A template can be inserted into the space having the same shape as the template. A molecule having a different stereo-structure from the template cannot be inserted into the space. Accordingly, it is possible to separate various molecules, which are different from a template, by using a polymer having a template space. This is the same theory as the Fischer's Lock-and-Key Concept that an antibody formed against an antigen selectively interacts only with the antigen, or the Receptor Theory that an enzyme in a body exhibits activity only to a certain substrate. Many researches for the molecularly imprinting technique have been performed in the field of a system for sensing or separating a certain material using a molecularly imprinted polymer.

In an illustrative embodiment, the pentraxin protein may be one pentraxin protein selected from the group consisting of a C-reactive protein, a serum amyloid P component, and PTX-3 (Pentraxin 3). Preferably, the pentraxin protein may be, but is not limited to, the C-reactive protein. The "C-reactive protein (CRP)" is one of plasma proteins that significantly increase in inflammatory diseases or diseases such as necrosis of body tissues, and a representative component of a so-called acute phase reactive protein. In case of occurrence of a problem in a body, the CRP increases in a short time from about 6 to about 24 hours. In recovery of a lesion, the CRP rapidly declines and disappears in a short time within about 24 hours. Accordingly, the CRP exhibits characteristics that cannot be seen in a general immune globulin antibody. As such, CRP measurement is useful for diagnosis of existence of an inflammatory or historrhexis disease and the severity thereof, disease progress monitoring, and prognosis prediction.

In an illustrative embodiment, if the pentraxin protein is the C-reactive protein, the ligand (L) of the pentraxin protein may be, but is not limited to, phophocholine. If the pentraxin protein may be the serum amyloid P component, the ligand (L) of the pentraxin protein may be, but is not limited to, proline. If the pentraxin protein is PTX-3, the ligand (L) of the pentraxin protein may be, but is not limited to, C1q (18 amino acids). For example, if the pentraxin protein is a C-reactive protein, two calcium divalent ions are bound to each monomer. A phosphate group of phosphorylcholine is bound to the monomer, having high selectivity. It is possible to prepare a reactive ligand capable of detecting each pentraxin protein by using the above-described ligands according to a chemical method well-known in the art.

In an illustrative embodiment, a molecularly imprinted structure for detection of a pentraxin protein is prepared by using a C-reactive protein that is one of the pentraxin proteins. However, it obvious to one of ordinary skill in art that for the other pentraxin proteins, a molecularly imprinted structure can be prepared in the same manner as described above.

Hereinafter, the method for preparing the molecularly imprinted structure using the C-reactive protein according to an embodiment will be described.

In an illustrative embodiment, a schematic method for polymerizing a support in situ is illustrated in FIG. 4. Basically, a C-reactive protein, which is one of pentraxin proteins, and a styrene-phosphocholine ligand, which is a reactive ligand of the C-reactive protein, are reacted with each other in advance. Thereafter, the reacting material is added to a buffer solution containing a crosslink agent and an initiator to synthesize a molecularly imprinted polymer through a photo-polymerization reaction. In another illustrative embodiment, a schematic method for separately preparing the support and then binding the support to the reactive ligand is illustrated in FIG. 6. The C-reactive protein, which is one of pentraxin proteins, and the styrene-phosphocholine ligand, which is a reactive ligand of the C-reactive protein, are reacted with each other in advance. Thereafter, the reacting material is chemically bound to a separately prepared support in a film, single layer, or particle form.

In an illustrative embodiment, the reactive group (R) may be, but is not limited to, a polymerizable group or a functional group reacting with metal or a metal oxide.

The polymerizable group may be, but is not limited to, a radical polymerization monomer selected from vinyl, styryl, acryloyl, methacryloyl, itaconoyl, sorbyl, and dienoyl. In an example, styrene is used as the polymerizable group.

The functional group reacting with metal or a metal oxide may be a metal reactive group selected, from thiol, disulfide, and thioether, or a metal oxide reactive group selected from trichlorosilyl, trimethylsilyl, triisopropylsilyl, and catechol. However, the present disclosure is not limited thereto.

In an illustrative embodiment, the linker (S) may be, but is not limited to, alkyl, aryl, arylalkyl, oligoethylene oxide, or a combination thereof. However, the present disclosure is not limited thereto. Length of carbon chains of the linker (S) may be, but is not limited to properly selected, for example, in a range of C3 to C20, to create flexibility between the ligand (L) and the reactive group (R). In an example, alkylcarboxylic ester is used as the linker.

In an illustrative embodiment, the reactive surface may be, but is not limited to, a surface of a film, nano-particles, a nano-wire, or porous particles formed of an organic or metallic material.

In an illustrative embodiment, the chemical reaction may be, but is not limited to, a polymerization reaction of a monomer and a crosslink agent with a reactive group of a reactive ligand, or a chemical binding reaction of metal or a metal oxide with a reactive group of a reactive ligand.

For example, the polymerization reaction may be, but is not limited to, a thermal polymerization or a photo-polymerization reaction by a radical polymerization initiator or a photo-polymerization initiator.

For example, the chemical binding reaction may be, but is not limited to, a binding reaction between thiol and gold particles or between trichlorosilyl and a metal oxide.

In accordance with another aspect of the present disclosure, there is provided a method for preparing a molecularly imprinted structure for detection of a pentraxin protein, wherein the pentraxin protein is a C-reactive protein, and the method includes:

(a) preparing a styrene-phosphocholine ligand, in which styrene and phosphocholine ligand are bound to each other;
(b) reacting the styrene-phosphocholine ligand with a C-reactive protein;
(c) adding the reacting material to a buffer solution containing a monomer, a crosslink agent, and an initiator and mixing them;
(d) performing a UV photo-polymerization reaction for the mixture to obtain a polystyrene polymer to which the C-reactive protein is bound; and
(e) removing the C-reactive protein by washing the polystyrene polymer with an elution buffer solution.

In an illustrative embodiment, the styrene-phophocholine ligand of the above step (a) is 12-(4-vinylbenzyl)oxycarbonyl dodecyl phosphocholine prepared according to reaction steps illustrated in FIG. 2 (refer to Example 1).

In an illustrative embodiment, the C-reactive protein and the styrene-phosphocholine ligand of the above step (b) are reacted with a molar ratio of about 1:3 to about 1:7, and preferably a molar ratio of about 1:5.

In an illustrative embodiment, in the above step (c), the monomer and the crosslink agent are styrene/DVB (divinylbenzene), and the initiator is DBK (dibenzylketone).

In an illustrative embodiment, the monomer, the crosslink agent, and the initiator may be mixed with a mixing ratio of about 8 to 18:1:1 to 5. In the illustrative embodiment, styrene, DVB, and DBK are mixed with a mixing ratio of about 9:1:1.

In an illustrative embodiment, the photo-polymerization reaction of the above step (d) is performed by performing a UV photo-polymerization reaction at about 35° C. to about 40° C. for about 1 to about 3 hours, and then, performing a UV photo-polymerization reaction at about 80° C. to about 100° C. for about 1 to about 3 hours.

In accordance with another aspect of the present disclosure, there is provided a reactive ligand capable of binding to a pentraxin protein, the reactive ligand having the following structural formula:

L—S—R [Structural Formula]

L: Ligand for binding with the pentraxin protein
R: Reactive group
S: Linker for linking between the ligand for binding with the pentraxin protein and the reactive group In accordance with another aspect of the present disclosure, there is provided a molecularly imprinted structure for detection of a pentraxin protein, the molecularly imprinted structure including a support and a multiple number of reactive ligands bound to a reactive surface of the support, wherein the multiple number of the reactive ligands are molecularly imprinted to be bound to the pentraxin protein.

In accordance with another aspect of the present disclosure, there is provided a chip for detection of a C-reactive protein, the chip including: a fixing layer formed on a metal substrate and having an azide or an acetylene end group $R^1$; and a molecularly imprinted layer formed on the fixing layer and including $R^2$—X-phosphocholine (wherein $R^2$ is an azide or an acetylene end group, and X is a spacer group having a length of about 0.1 nm to about 5 nm), wherein the phophocholine group included in the molecularly imprinted layer is arranged to correspond to a phosphocholine binding site of each molecule of the C-reactive protein, and the fixing layer and the molecularly imprinted layer may be bound to each other through a click chemistry reaction between the end group $R^1$ of the fixing layer and $R^2$ included in $R^2$—X-phosphocholine of the molecularly imprinted layer.

In an illustrative embodiment, if the end group $R^1$ of the fixing layer is the azide group, $R^2$ of the molecularly imprinted layer may be the acetylene group. If the end group $R^1$ of the fixing layer is the acetylene group, $R^2$ of the molecularly imprinted layer may be the azide group. However, the present disclosure is not limited thereto.

A target material desired to be sensed in an illustrative embodiment is the C-reactive protein. The C-reactive protein is one of proteins observed in blood. Since the C-reactive protein increases in case of existence of inflammation, it is used as a marker for inflammation. The physiological function of the C-reactive protein relates to binding with phosphocholines presented on surfaces of cells (and some types of bacteria) that are dead or dying to activate a complement system, through a C1Q complex (antigen+antibody). The C-reactive protein raises phagocytosis of macrophages expressing a receptor of the CRP. Each of molecules of the C-reactive protein has their binding sites that can be specifically bound to five phosphocholine groups.

In the chip for detection of the C-reactive protein in accordance with an illustrative embodiment, an end of the molecularly imprinted layer is arranged such that the five phosphocholine groups correspond to phosphocholine binding sites of respective molecules of the C-reactive protein.

In an illustrative embodiment, the fixing layer may be, but is not limited to, a polymer layer, a self assembled monolayer, or mica, having an azide or acetylene end group $R^1$ on the surface thereof. For example, the polymer layer, the self assembled monolayer, or the mica is fixed on the metal substrate through a thiol group. The surface thereof may have azide or acetylene group or may be modified through proper surface treatment to have azide or acetylene group. However, the present disclosure is not limited thereto.

Any polymer layer may be used if it is fixed on the metal substrate through a functional group such as a thiol group, and the surface thereof has an azide or acetylene group. For example, the polymer layer may be formed including, but is not limited to, polyacrylate, polymethacrylate, ethylene glycol amine, ethyleneglycolthiol, NHS(Nhydroxysuccinimide)-ethylene glycol, maleimide-ethylene glycol, polyethylene glycol amine, polyethylene glycol thiol, (NHS)-polyethylene glycol, maleimide-polyethylene glycol, polymer based on carbohydrate monomer binding, and a combination thereof.

In an illustrative embodiment, the self assembled monolayer may be formed including, but is not limited to, HS—Y—$R^1$ (wherein $R^1$ is an azide or acetylene end group, and Y is a spacer group having a length of about 0.1 nm to about 5 nm).

In an illustrative embodiment, the spacer group Y in HS—Y—$R^1$ for formation of the self assembled monolayer may be, but is not limited to, a hydrocarbon group or an oxyhydrocarbon group, which may include at least one of double binding, triple binding, and an aromatic ring and have about 1 to about 30 carbons. For example, the spacer group Y may be a hydrocarbon group or an oxyhydrocarbon group, which may include at least one of double binding, triple binding, and an aromatic ring and have about 1 to about 30 carbons, about 1 to about 25 carbons, about 1 to about 20 carbons, or about 1 to about 15 carbons. However, the present disclosure is not limited thereto. In an illustrative embodiment, the spacer group Y may be an alkylene group or alkyleneoxide (e.g., polyethyleneoxide and a polyprophyleneoxide group), which may include at least one of double binding, triple binding, and an aromatic ring and have about 1 to about 30 carbons, about 1 to about 25 carbons, about 1 to about 20 carbons, or about 1 to about 15 carbons. However, the present disclosure is not limited thereto. For example, the self assembled monolayer may be formed including, but is not limited to, azido-$C_{1-30}$alkylene-1-thiol, acetylene-$C_{1-30}$alkylene-1-thiol, or propargyloxy-$C_{1-30}$alkylene-1-thiol.

In an illustrative embodiment, a material for the metal substrate is not particularly limited. Any material may be used if it is generally used in the art to prepare a chip for detection of the C-reactive protein. For example, the metal substrate may be formed of, but is not limited to, gold, silver, copper, or palladium, and more preferably, gold (Au).

In an illustrative embodiment, the molecularly imprinted layer may be formed including, but is not limited to, $R^2$—X-phosphocholine (wherein $R^2$ is an azide or acetylene end group, and X is a spacer group having a length of about 0.1 nm to 5 nm). In an illustrative embodiment, the molecularly imprinted layer may be formed including, but is not limited to, acetylene-$C_{1-30}$alkylene-phosphorylcholine, propargyloxy-$C_{1-30}$alkylene-phosphorylcholine, or azido-$C_{1-30}$alkylene-phosphorylcholine.

As described above, the azide or the acetylene end self assembled monolayer is formed by fixing on the metal substrate through a functional group capable of being bound to metal such as a thiol group. A molecularly imprinted layer is formed on the azide or the acetylene end-self assembled monolayer through a click chemistry reaction. In this manner, it is possible to prepare the chip for detection of the C-reactive protein, facilitating fixing a molecularly imprinted layer on the metal substrate and improving a constant for binding to the C-reactive protein thereby providing an improved detection effect. The chip for detection of the C-reactive protein in accordance with an illustrative embodiment exhibits a high constant for binding to the C-reactive protein. Accordingly, a low concentration of the C-reactive protein can also be detected, so that a concentration of the C-reactive protein in serums can also be measured by using surface Plasmon resonance. Since the click chemistry reaction is pH-independent, very fast, and effective, it enables the molecularly imprinted layer to be easily and effectively fixed onto the metal substrate. Accordingly, in an illustrative embodiment, it is possible to easily prepare the chip for detection of the C-reactive protein without using an antibody.

A method for preparing a chip for detection of a C-reactive protein in accordance with another aspect of an illustrative embodiment may include:

forming a fixing layer having the azide or the acetylene end group $R^1$ on a metal substrate; mixing the C-reactive protein and a molecularly imprinted material including $R^2$—X-phosphocholine (wherein $R^2$ is azide or acetylene end group, and X is a spacer group having a length of about 0.1 nm to about 5 nm) to obtain a mixture solution of the molecularly imprinted material/the C-reactive protein; immersing the metal substrate, on which the fixing layer is formed, in the mixture solution of the molecularly imprinted material/the C-reactive protein to obtain a complex layer of the metal substrate/the fixing layer/the molecularly imprinted material/the C-reactive protein through a click chemistry reaction between the end group $R^1$ of the fixing layer and $R^2$ included in $R^2$—X-phosphocholine of the molecularly imprinted material; and removing the C-reactive protein from the complex layer to obtain a molecularly imprinted layer.

In an illustrative embodiment, if the end group $R^1$ of the fixing layer is an azide group, $R^2$ of the molecularly imprinted material may be an acetylene group. If the end group $R^1$ of the fixing layer is an acetylene group, $R^2$ of the molecularly imprinted material may be an azide group. However, the present disclosure is not limited thereto.

In an embodiment of the present disclosure, the fixing layer may be, but is not limited to, a polymer layer, a self assembled monolayer, or a mica, having an azide or acetylene end group $R^1$ on the surface thereof.

The above-described preparing method may further include reacting propagyl alcohol on a portion of the fixing layer, which has not been bound to the molecularly imprinted material, after formation of the complex layer. However, the present disclosure is not limited thereto.

In an illustrative embodiment, the above-described preparing method may further include pre-culturing the mixture solution of the molecularly imprinted material/the C-reactive protein, prior to immersing the metal substrate on which the fixing layer is formed, such that five phosphocholine groups derived from the molecularly imprinted material are arranged to correspond to phophocholine binding sites of respective molecules of the C-reactive protein. However, the present disclosure is not limited thereto.

In an illustrative embodiment, the molecularly imprinted material and the C-reactive protein may be mixed with an equivalent ratio of about 5:about 1. However, the present disclosure is not limited thereto. For example, each of molecules of the C-reactive protein has their respective phosphocholine binding sites capable of being bound to five phosphocholine groups. Accordingly, if the molecularly imprinted material and the C-reactive protein are mixed with the above-described equivalent ratio for reaction or pre-culture, the molecularly imprinted material is bound to the phosphocholine binding sites of the C-reactive protein, so that the phosphocoline groups of the molecularly imprinted material can be arranged to correspond to the phosphocholine binding sites of the C-reactive protein.

The descriptions of the chip for detection of the C-reactive protein in accordance with an aspect of the present disclosure are applied to the method for preparing a chip for detection of a C-reactive protein in accordance with an illustrative embodiment. Thus, for convenience sake, overlapping descriptions in this regard are omitted herein.

Another aspect of the present disclosure provides a surface Plasmon resonance sensor, including the chip for detection of the C-reactive protein as stated as above. The descriptions of the chip for detection of the C-reactive protein and the method for preparing the same are applied to the surface Plasmon resonance sensor. For convenience sake, overlapping descriptions in this regard are omitted herein.

BRIEF DESCRIPTION OF THE DRAWINGS

Non-limiting and non-exhaustive embodiments will be described in conjunction with the accompanying drawings. Understanding that these drawings depict only several embodiments in accordance with the disclosure and are, therefore, not to be intended to limit its scope, the disclosure will be described with specificity and detail through use of the accompanying drawings, in which.

DETAILED DESCRIPTION OF THE INVENTION

Hereinafter, illustrative embodiments will be described in more detail with reference to illustrative working examples. The illustrative working examples are merely exemplary, and the scope of the present disclosure should not be construed as being limited to the illustrative working examples.

Example 1

Preparation of a Styrene-Phosphocholine Ligand

Figure 1:
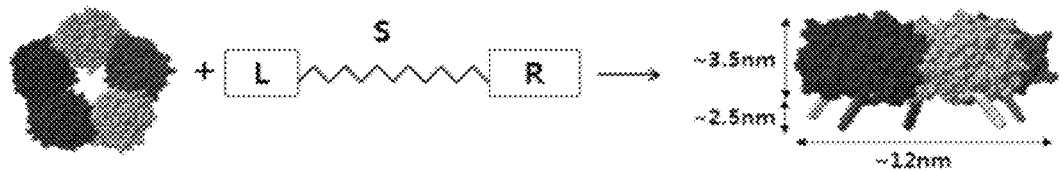
FIG. 1 is a view schematically illustrating a process of binding between a pentraxin protein and a reactive ligand according to an illustrative embodiment.
Figure 2:
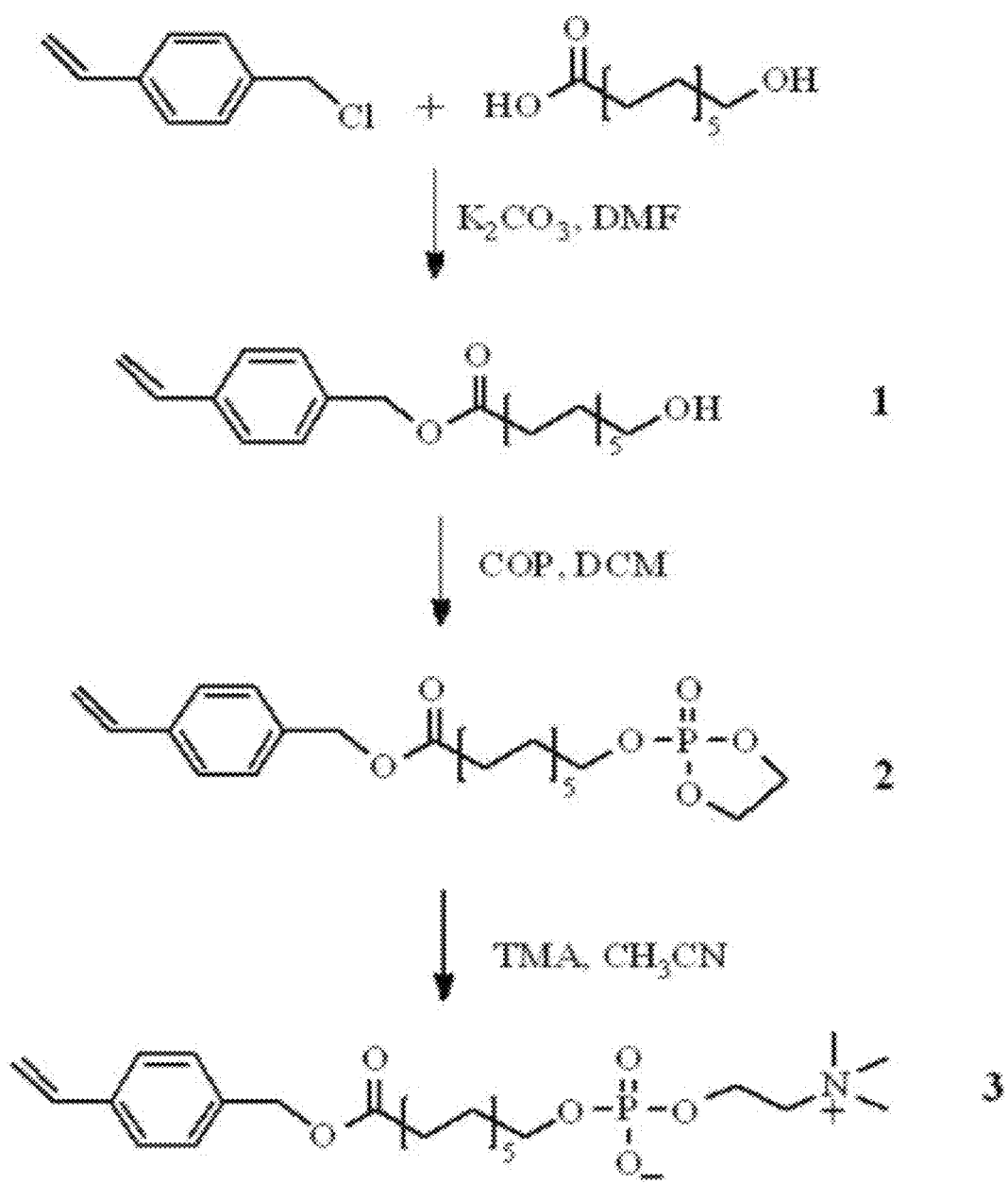
FIG. 2 is a view for explanation of a method for preparing a styrene-phosphocholine ligand by steps according to an illustrative embodiment.
Figure 3:
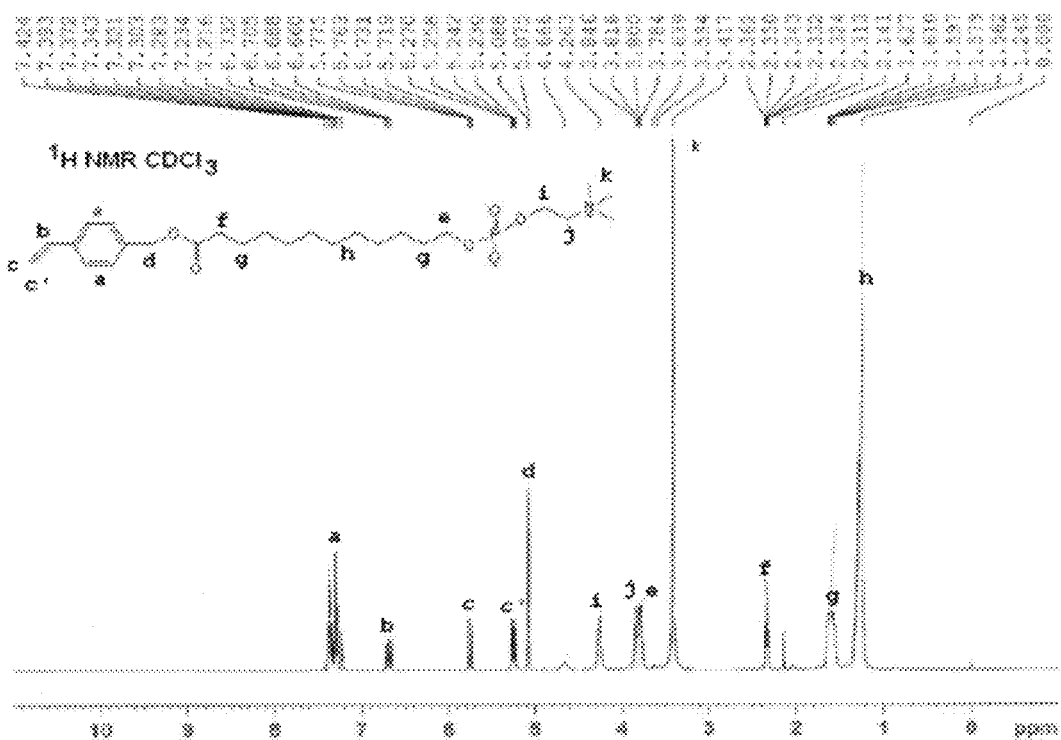
FIG. 3 is NMR analysis results for a styrene-phosphocholine ligand prepared according to an illustrative working example.

A process for preparing a styrene-phosphocholine ligand was described below with reference to FIG. 2. The products presented in FIG. 2 have been identified through NMR.

12-hydroxydecanoic acid and potassium carbonate were added into 100 ml of N,N'-dimethylformamide and stirred at a room temperature for about 10 minutes. Thereafter, 4-vinylbenzyl chloride was added thereinto and stirred while being heated at less than about 80° C. After the reaction was finished, N,N'-dimethylformamide was removed through distillation under reduced pressure. The reacting material was dissolved in dichloromethane and then washed with water. Dichloromethane layers were collected and dried with a magnesium sulfate. From the dried dichloromethane, the magnesium sulfate was removed by a depressurization filter, and dichloromethane was removed through distillation under reduced pressure. Thereafter, column chromatography purification using an eluent of hexane and ethyl acetate with a ratio of 3:1 was performed (yield=79%).

$_1$H NMR (CDCl$_3$ 400 MHz): δ (ppm) 7.41 (m 4H), 6.75 (m 1H), 5.78 (dd J$_1$=13.6 J$_2$=4.0 $_1$H), 5.29 (d$_d$ J1=6.8 J2=4.0 1H), 5.10 (d J=7.2 2H), 3.63 (t J=4.4 2H), 2.$_3$7 (t J=4.8 2H), 1.64 (m 4H), 1.27 (br s 14H)

$_{13}$C NMR (CDCl$_3$ 100 MHz): δ (ppm) 173.74, 137.90, 137.52, 136.47, 136.40, 136.35, 135.62, 128.77, 128.47, 127.60, 126.36, 126.05, 126.01, 114.39, 114.30, 65.97, 65.83, 63.11, 34.35, 32.81, 29.56, 29.49, 29.41, 29.24, 29.12, 25.74, 24.96

LRMS (ESI+) m/z: 355 (M+Na)

FT-IR (neat) ν (cm$_{-1}$): 3328 (br w), 2914 (s), 2848 (s), 1728 (s), 1462 (m), 1386 (w), 1359 (w), 1332 (m), 1316 (w), 1256 (m), 1195 (s), 1107 (m), 1057 (m), 1042 (m), 1008 (m), 989 (m), 962 (m), 899 (m), 830 (w), 850 (w), 804 (m), 728 (m)

1.5 g of 4-Vinylbenzyl-12-hydroxyl dodecanoate (496 mmol) and 2.09 ml of triethylamine (14.9 mmol) were added into 20 ml of dichloromethane (amylene stabilized) and stirred while being cooled at 0° C. on an ice-bath. 0.684 ml of 2-chloro-2-oxo-1,3,2-dioxaphospholane (7.44 mmol) was added into the reacting material and stirred at 0° C. for about 1 hour. Thereafter, the ice-bath was removed, and the reacting material was reacted at a room temperature. After the reaction was finished, dichloromethane was removed through distillation under reduced pressure. The reacting material was dissolved in chloroform and undissolved solids were removed by means of a depressurization filter. Column chromatography purification using an eluent of hexane and ethyl acetate with a ratio of 3:1 was performed (since the intermediate compound was easily denatured, a next follow-up reaction was proceeded with after identification of $_1$H NMR). 0.864 g of 12-(2-Oxo-2λ5-[1,3,2]dioxaphospholan-2-yloxy)-dodecanoic acid 4-vinyl-benzyl ester (1.97 mmol) were added into a pressure bottle together with an acetonitrile anhydrous and cooled to −20° C. 0.55 ml of trimethylamine (5.92 mmol) was added into the cooled pressure bottle and heated at less than 60° C. with stirring.

After the reaction was finished, acetonitrile was removed through distillation under reduced pressure. Column chromatography purification using an eluent of chloroform, methanol, and water with a ratio of 65:25:4 was performed (yield=24%).

$_1$H NMR (CDCl$_3$ 400 MHz): δ (ppm) 7.42 (m 4H), 6.73 (m 1H), 5.77 (dd J$_1$=13.6 J$_2$=4.0 1H), 5.27 (d$_d$ J1=6.8 J2=4.0 1H), 5.08 (d J=7.2 2H), 4.26 (br s 2H), 3.84 (m 4H), 3.41 (s 9H), 2.36 (m 2H), 1.62 ($_m$ 4H), 1.24 (br s 14H)

$_{13}$C NMR (CD$_c$13 100M$_{Hz}$): δ (ppm): 173.68, 137.87, 137.50, 136.46, 136.39, 136.33, 135.61, 128.77, 128.44, 127.57, 126.35, 126.01, 125.99, 114.39, 114.30, 66.25, 65.95, 65.81, 65.66, 65.60, 59.20, 54.29, 34.32, 31.07, 31.00, 29.70, 29.64, 29.53, 29.49, 29.32, 29.16, 25.92, 24.96

LRMS (ESI+) m/z: 520 (M+Na)

FT-IR (neat) υ (cm$_{-1}$): 3367 (br w), 2923 (s), 2852(m), 1732(s), 1483(w), 1380(w), 1232(s), 1164(s), 1057(s), 986(s), 966(s), 909(s), 874(w), 825(s), 796(s), 763(s), 713(s), 505(s)

Figure 4:
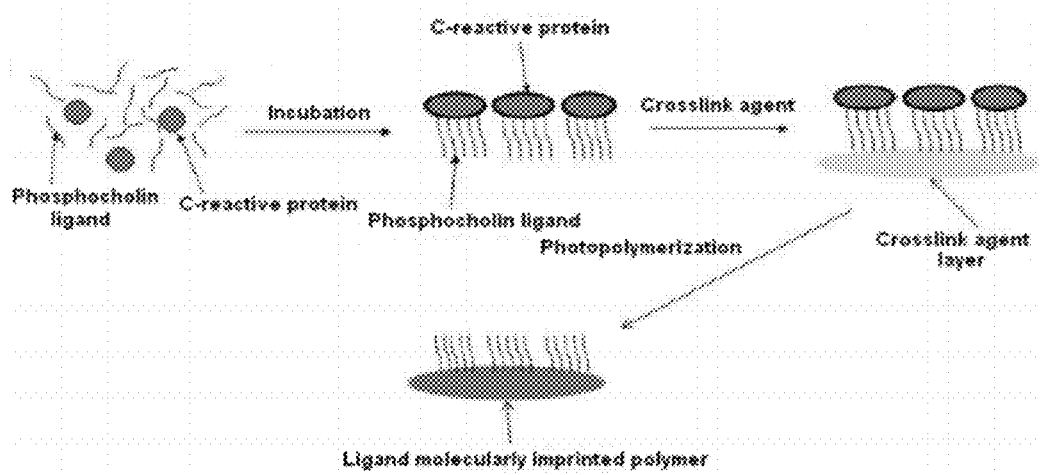
FIG. 4 is a schematic view showing a method for preparing a molecularly imprinted polymer using a styrene-phosphocholine ligand according to an example.

The styrene-phosphocholine ligand (12-(4-vinylbenzyl) oxycarbonyl dodecyl phosphocholine) that has been prepared as described above was identified as a final product by means of NMR (Nuclear Magnetic Resonance; Avance 400; the Bruker company). FIG. 4 shows results of the NMR analysis.

Example 2

Figure 5:
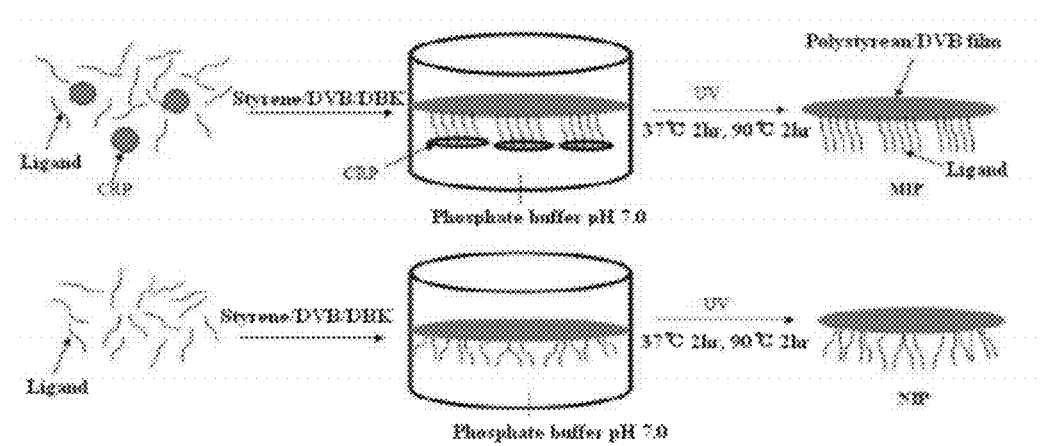
FIG. 5 is a schematic view showing a method for preparing a molecularly imprinted polystyrene film using a styrene-phosphocholine ligand according to an example.
Figure 6:
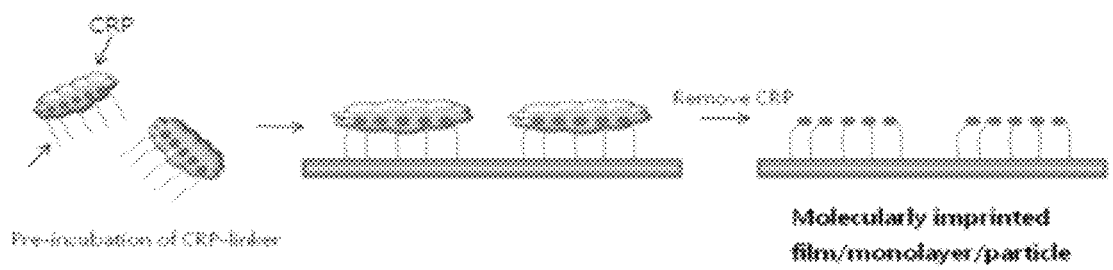
FIG. 6 is a schematic view showing a method for preparing a molecularly imprinted polymer using a styrene-phosphocholine ligand according to an example.

Preparation of a Polystyrene Film, in which a Styrene-Phophocholine Ligand is Molecularly Imprinted A method for preparing a molecularly imprinted polymer according to an illustrative embodiment is described below with reference to FIG. 5.

Total 1 ml of styrene/DVB(divinylbenzene) as a crosslink agent, and DBK(dibenzylketone) as an initiator, were added to 10 ml of a standard phosphate buffer solution (pH 7.0) with a ratio of styrene:DVB:DBK=9:1:1. Thereafter, a C-reactive protein and a styrene-phosphocholine ligand, which have been reacted together in advance, were added thereto with a molar ratio of 1:5. Since the C-reactive protein and the styrene-phosphocholine ligand were strongly bound to each other via calcium ions, they have been reacted in advance in a binding buffer solution (0.1M Tris, 5 mM CaCl$_2$, 150 mM NaCl, and pH 8.0) thereby inducing photo-polymerization thereafter. With respect to conditions for the polymerization reaction, photo-polymerization was performed at 37° C. for 2 hours such that a monomer (styrene-phophocholine ligand) is positioned on a surface of the crosslink agent layer in the state that the monomer is bound to the C-reactive protein (here, since the ligand has both a hydrophilic group and a hydrophobic group, the hydrophilic group is directed toward a water phase, and the hydrophobic group is directed toward a surface of styrene/DVB). Subsequently, photo-polymerization was performed at 90° C. for 2 hours such that a hard polystyrene polymer can be formed. After the polymerization reaction was finished, in order to remove the C-reactive protein, the reacting material was washed with an elution buffer solution (0.1 M Tris, 10 mM EDTA, 150 mM NaCl, pH 8.0) twice.

Experimental Example 1

Measurement of a Binding Force of a C-Reactive Protein to a Molecularly Imprinted Polymer A binding force of a C-reactive protein to a molecularly imprinted polymer was analyzed by detecting a C-reactive protein through the Bradford assay method and an immunoassay method. In this case, in addition to a molecularly imprinted polymer (MIP), a molecularly non-imprinted polymer (NIP) and a polystyrene polymer (control polymer; CP) were prepared to analyze a molecularly imprinting effect. The molecularly non-imprinted polymer was prepared by using a reactive ligand without molecularly imprinting of CRP. The polystyrene polymer was prepared without using a reactive ligand and CRP.

(1) Bradford Assay Method

5 μg of a CRP was added to the prepared molecularly imprinted polymer and reacted at 0° C. for 30 minutes. In order to remove a non-specifically bound protein, the reacting material was washed three times with PBS or repeatedly washed three times with a TBST buffer solution (0.1 M Tris, 150 mM NaCl, 0.1% Tween 20) containing 0.1% Tween 20. Thereafter, 2 ml of an elution buffer solution was added thereto, and the reacting material was kept at a room temperature for 15 minutes. In order to quantify an amount of the protein in the elution buffer solution, 1 ml of a Bradford reagent (the Sigma company) was added to 1 ml of an eluted protein solution, and the solution was kept at a room temperature for 10 minutes. Thereafter, absorbance was measured at 595 nm. In order to prepare a standard quantification curve, 0, 0.5, 1, 1.5, and 2 μg/ml of BSA solutions were prepared. 1 ml of the Bradford reagent was added to 1 ml of each of the BSA solutions, and the solution was kept at a room temperature for 10 minutes. Thereafter, absorbance was measured at 595 nm (Varian-300 spectrophotometer).

(2) Immunoassay Method

5 μg of a CRP was added to the prepared molecularly imprinted polymer and reacted at 0° C. for 30 minutes. In order to remove a non-specifically bound protein, the reacting material was washed three times with PBS or repeatedly washed three times with a TBST buffer solution (0.1 M Tris, 150 mM NaCl, 0.1% Tween 20) containing 0.1% Tween 20. Thereafter, 10 μg of anti CRP mouse monoclonal antibody (the Sigma company) was added thereto, and the reacting material was reacted at 0° C. for 30 minutes. In order to remove a non-specifically bound antibody, the reacting material was washed three times with PBS or repeatedly washed three times with a TBST buffer solution (0.1 M Tris, 150 mM NaCl, 0.1% Tween 20) containing 0.1% Tween 20. Thereafter, an anti mouse IgG (the Sigma company), to which alkaline phosphatase was bound, was diluted with a ratio of 1:30,000 and added thereto. Thereafter, the reacting material was reacted at 0° C. for 30 minutes. In order to remove a non-specifically bound antibody, the reacting material was washed three times with PBS or repeatedly washed three times with a TBST buffer solution (0.1 M Tris, 150 mM NaCl, 0.1% Tween 20) containing 0.1% Tween 20. Thereafter, 1 ml of an NPP solution (p-nitrophenolphosphate; the Sigma company), which is a substrate of alkali phosphatase, was added thereto, and the reacting material was kept at a room temperature for 10 minutes. Thereafter, absorbance was measured at 405 nm (Varian-300 spectrophotometer).

TABLE 1

Effect of molecularly imprinting a C-reactive protein

| | Assay method/Washing buffer | | | |
|---|---|---|---|---|
| | Bradford assay (μg) | | Immunoassay (O.D) | |
| Sample | PBS | TBST | PBS | TBST |
| CP | 0.45 ± 0.0073 | 0.13 ± 0.021 | — | — |
| NIP | 1.4 ± 0.051 | 0.27 ± 0.041 | 0.48 ± 0.061 | 0.024 ± 0.0051 |
| MIP | 3.0 ± 0.71 | 2.6 ± 0.17 | 1.3 ± 0.18 | 0.19 ± 0.061 |
| IF | 2.1 | 9.8 | 2.6 | 8.1 |

Table 1 shows comparison of molecularly imprinting factors (imprinting factor; IF) of C-reactive proteins of a MIP and a NIP. An amount of a C-reactive protein bound to the MIP was higher 8.1 or 9.8 times than an amount of a C-reactive protein bound to the NIP depending on a test method. It is understood that the C-reactive protein on the NIP was eluted during the washing process, whereas the C-reactive protein on the MIP was not eluted and remains.

Experimental Example 2

Determination of a Binding Constant to a MIP

Figure 7:
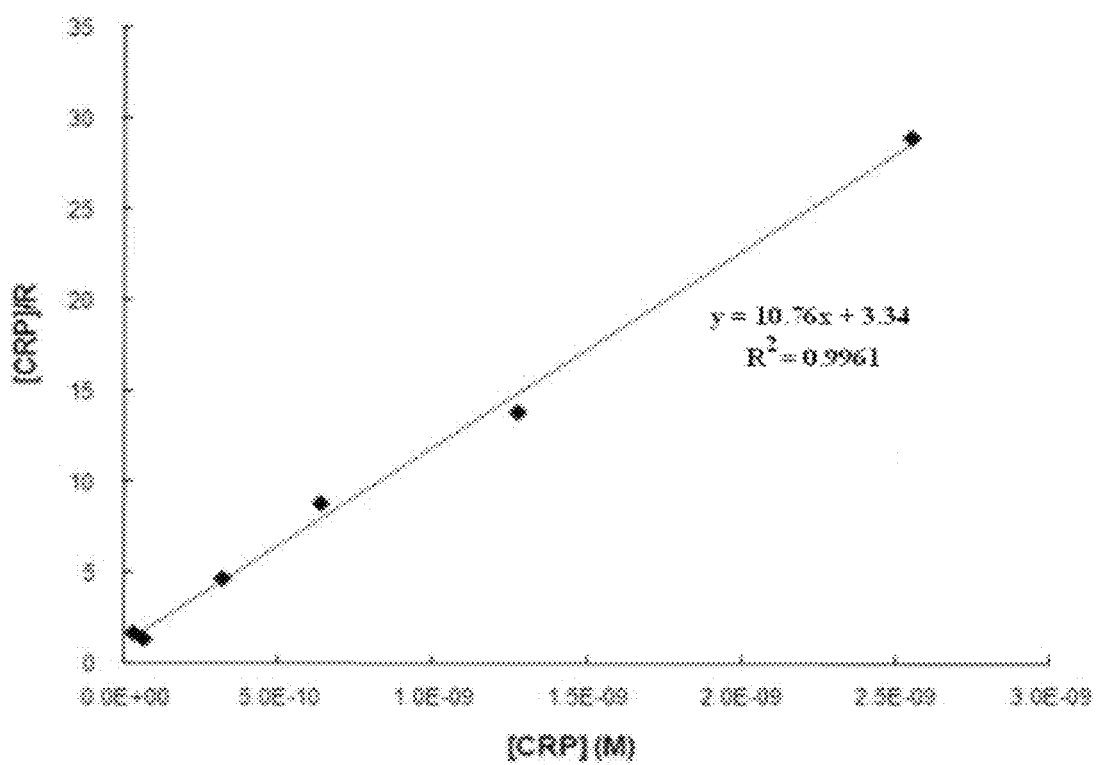
FIG. 7 is a graph showing Langmuir plot to determine a binding constant for a MIP in an example.

FIG. 7 is a graph using the Langmuir isotherm equation. Based on slope and a y-intercept value, a MIP-C-reactive protein binding constant $K_A$ is $3.0 \times 10^9$/M. Below is the Langmuir isotherm equation:

$$\frac{C}{R} = \frac{C}{R_{max}} + \frac{1}{R_{max}} \times \frac{1}{K_A}$$

$R_{max}$ can be calculated from a reciprocal number of the slope, and $K_A$ can be calculated from the y-intercept.

Following table 2 shows CRP binding constants that have been reported until now. The detection method using a molecularly imprinted polymer in an illustrative embodiment exhibits a binding constant value higher about three degrees than that in detection methods using a conventional anti C-reactive protein antibody.

TABLE 2

Comparison of binding constants in the detection method of an illustrative embodiment and a conventional detection method

| Receptor | Detection method | Binding constant ($K_A$, M$^{-1}$) | Reference |
|---|---|---|---|
| Anti-CRP antibody (immobilized) | SPR | $1.4 \times 10^6$ | 1 |
| Anti-CRP antibody (immobilized) | fiber-optic detection | $3.8 \times 10^8$ | 2 |
| Exposed PC on supported lipid monolayers[a] | SPR | $9.9 \times 10^6$ | 3 |
| PC-appended supramolecular assembly | ELISA | $7.1 \times 10^6$ | 4 |
| The MIP in this study | MSIA | $3.0 \times 10^9$ | — |

1. M. H. F. Meyer, M. Hartmann and M. Keusgen, *Biosens. Bioelectron.*, 2006, 21, 1987
2. C. Chou, H. Y. Hsu, H. T. Wu, K. Y. Tseng, A. Chiou, C. J. Yu, Z. Y. Lee and T. S. Chan, *J. Biomed. Opt.*, 2007, 12, 024025
3. S. F. Sui, Y. T. Sun and L. Z. Mi, *Biophys. J.*, 1999, 76, 333;
4. B. A. Rosenzweig, N. T. Ross, D. M. Tagore, J. Jayawickramarajah, I. Saraogi and A. D. Hamilton, *J. Am. Chem. Soc.*, 2009, 131, 5020.

Experimental Example 3

Analysis of a Selective Binding Force of a MIP

In order to identify a specific binding force of a MIP to a CRP, 5 μg of bovine serum albumin (BSA) and 5 μg of carbonic anhydrase (CA) were added into each of the MIP and the NIP. The binding force was analyzed in the same manner as described in Experimental Example 1.

Figure 8:
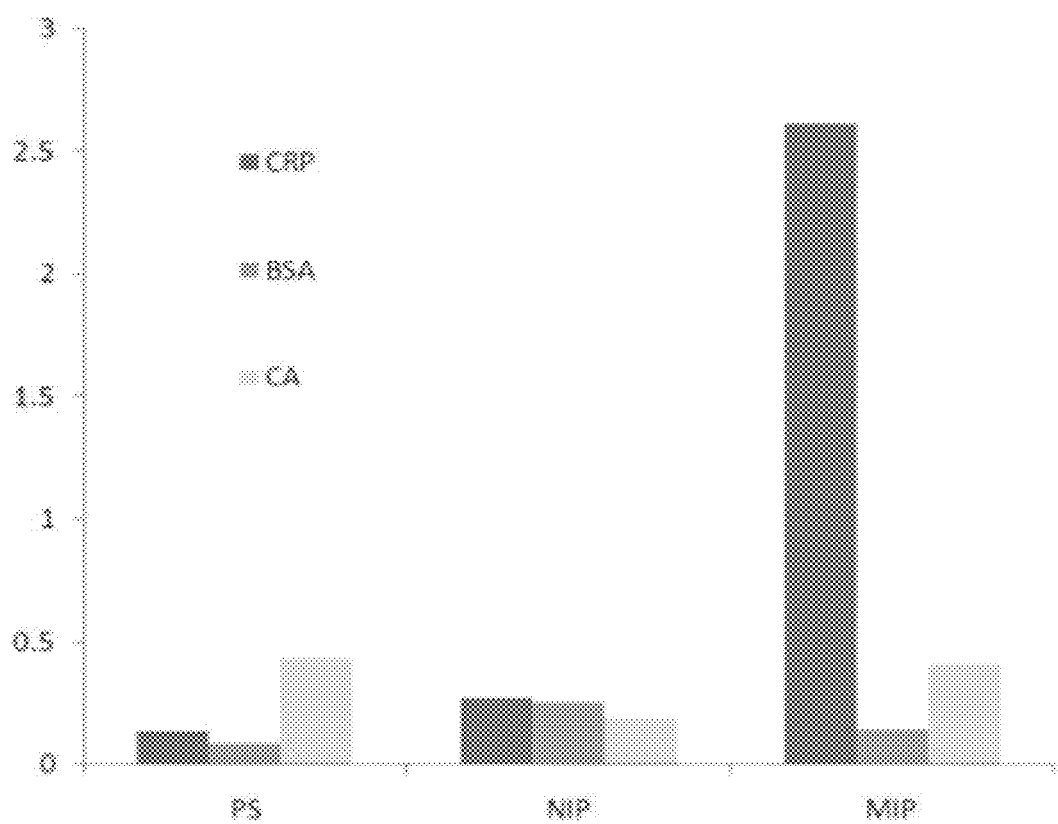
FIG. 8 shows analysis results for a selective binding force of a MIP using BSA and CA.

FIG. 8 shows binding forces of the MIP and the NIP to BSA and CA. As shown in FIG. 8, the PS and the NIP exhibit a low binding force of less than 0.5 μg to the CRP, BSA, and CA. However, the MIP exhibits a higher binding force of more than 2.5 μg only to the C-reactive protein. It shows that the MIP was specifically bound to the CRP.

Experimental Example 4

AFM Analysis

Figure 9:
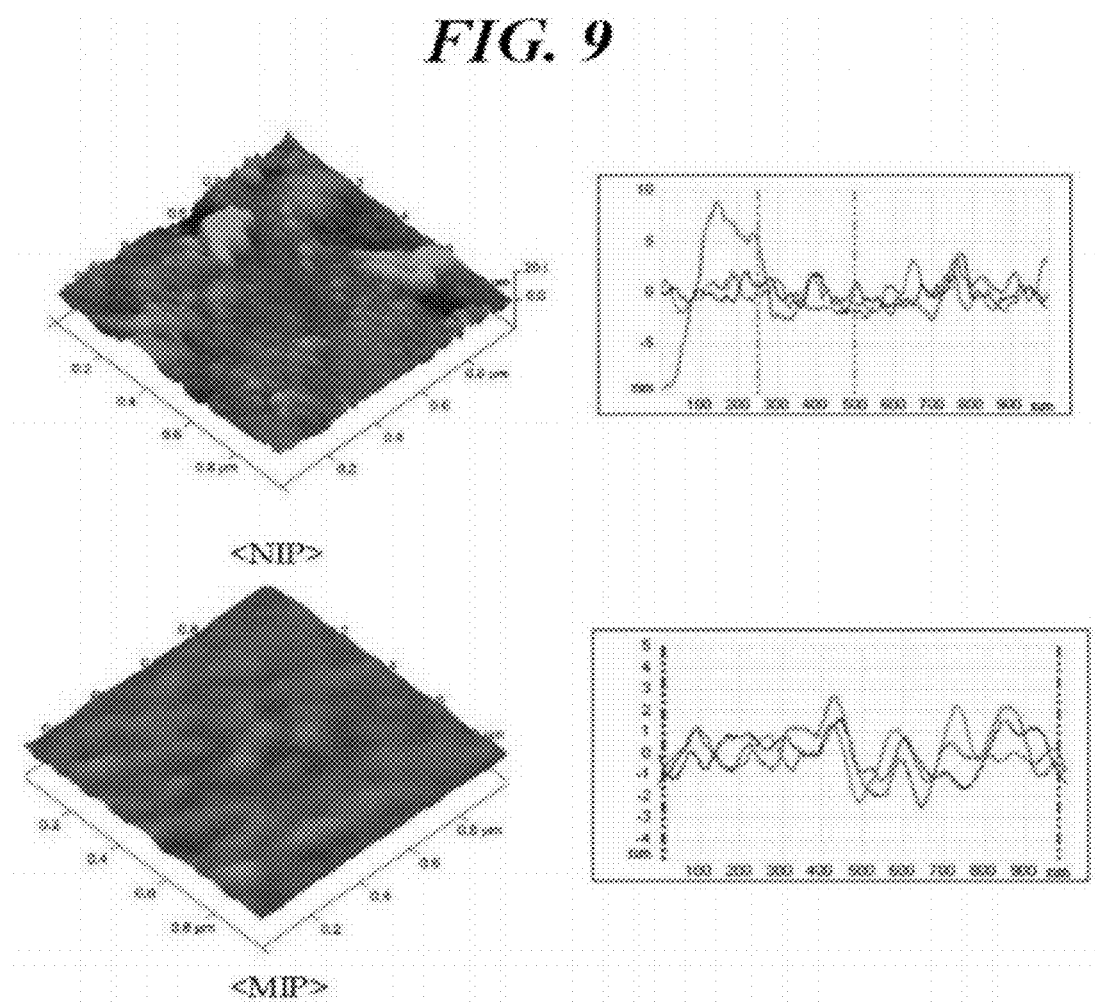
FIG. 9 shows observation results for distribution of C-reactive proteins being bound to a NIP, which is a control group of a MIP, by means of AFM in an example.

FIG. 9 shows observance results for distribution of C-reactive proteins being bound to a MIP and a NIP by means of an atomic force microscope (AFM; the Vecco company; model code: D-V). Upon observation, the height of a side surface of the protein on the MIP is relatively regular, while the protein on the NIP is partially agglutinated or bound with its side surface having irregular height. In case of the molecularly imprinted protein, pentamers are simultaneously bound thereby exhibiting a plane and regular height of the side surface. However, on the surface of the molecularly non-imprinted polymer, binding through only one ligand is possible. Accordingly, the protein binding shape and the protein distribution were irregular, which were different from those in the MIP.

Example 3

Preparation of a Polystyrene Bead, in which a Functional Monomer is Molecularly Imprinted A process for preparing a molecularly imprinted polystyrene bead was the same as Example 1. However, in order to disperse styrene/DVB on an aqueous solution, 0.1% Brij 78 was added as a dispersant, and then, photo-polymerization was performed. Under the same conditions as those in Example 2, the 0.1% Brij 78 dispersant was added, such that styrene/DVB was dispersed in a bead form through vigorous stirring. During the photo-polymerization, styrene/DVB was continuously dispersed through stirring.

Figure 10:
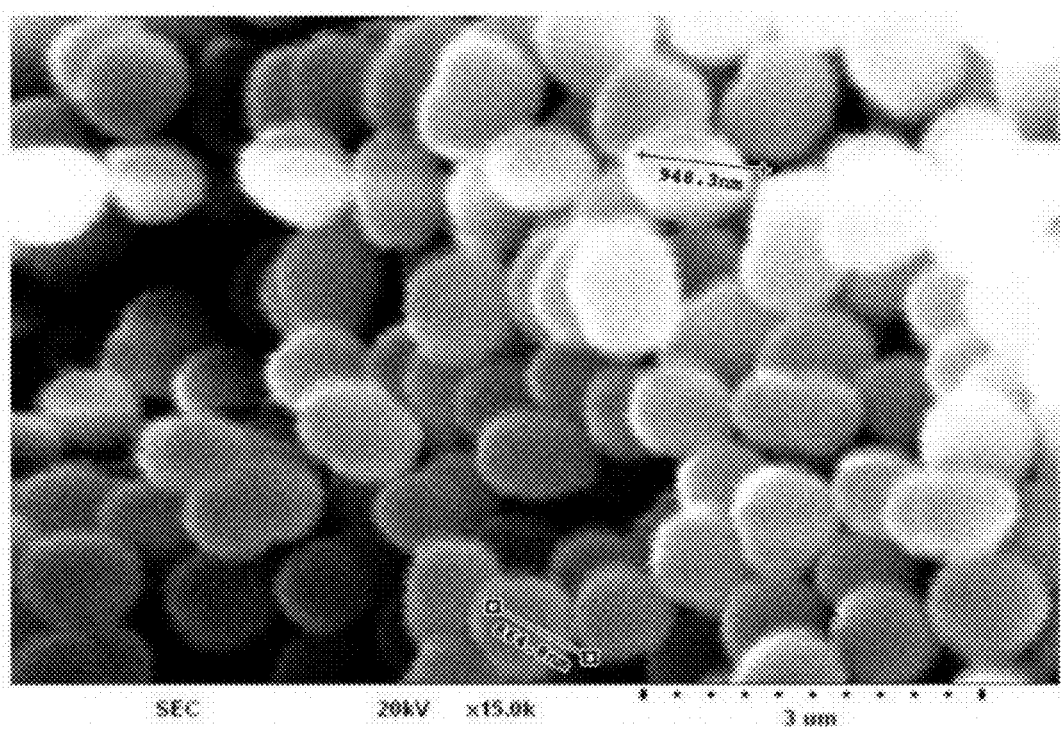
FIG. 10 is a microphotograph obtained by observing a polystyrene bead prepared according to an example by means of SEM.
Figure 11A:
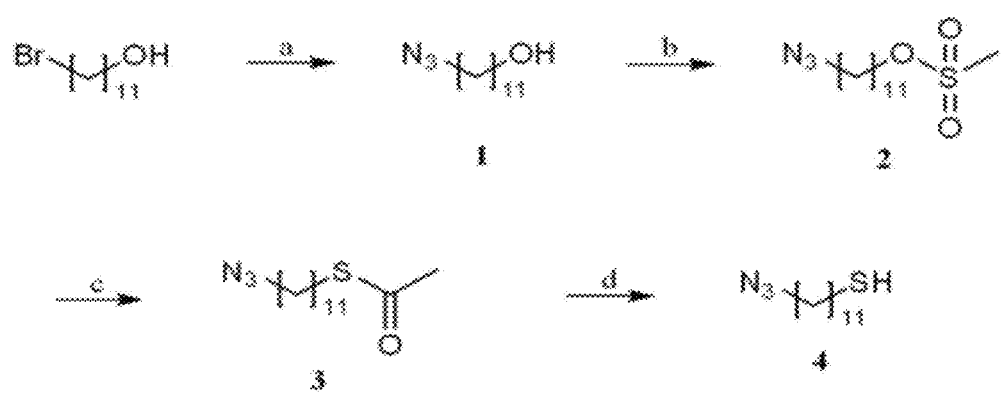
FIG. 11 is a chemical formula showing a method for preparing (a) 11-azidoundecane-1-thiol (azido-thiol) and (b) 6-propargylhexylphosphorylcholine (propargyl-PC) in an example.
Figure 11B:
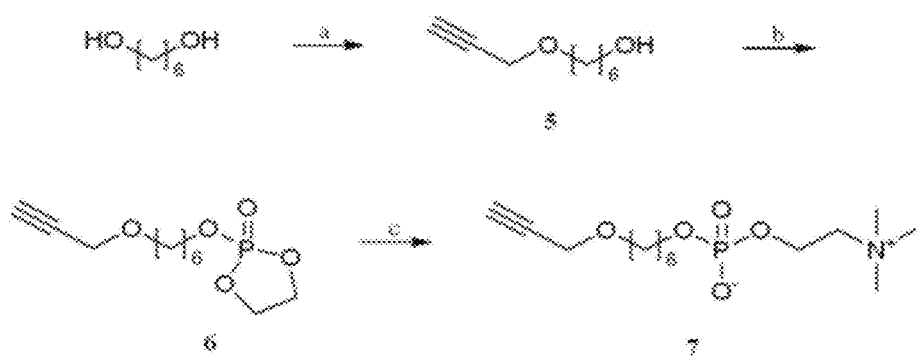

FIG. 10 shows results of observation of the prepared polystyrene bead by means of an SEM. The size of the bead is in a range of 1.2 μm to 1.8 μm. A molecularly imprinting factor is 3.6. A detection limit, which can be identified by the Bradford assay method, is 0.3±0.1 μg/ml. Accordingly, CRP detection is possible at a concentration below a blood concentration range. Upon measurement of surface conductivity, the surface conductivity of the polystyrene bead, to which no ligand is bound, is 0.0767 mS/cm. The surface conductivity of the bead, in which a ligand is molecularly imprinted, is 9.98 mS/cm. Since one end of the reactive ligand has a choline group and a phosphate group, they exhibit + and − charges. For this reason, the surface conductivity of the bead in which a ligand is molecularly imprinted appears to have increased, compared to that of the polystyrene bead to which no ligand is bound.

Example 4

Synthesis of 11-Azidoundecane-1-Thiol

All reagents for chemical synthesis were purchased from Sigma-Aldrich Chemical and used without additional purification. Human plasma and all buffer components were also purchased from Sigma-Aldrich Chemical. For a CRP-negative human serum (N-serum), components of the CRPA Latex Test Set purchased from Cenogenics (Morganville, USA) were used. Phosphate buffered saline (PBS) and HyClone(R) were purchased from Thermo Scientific (Rochester, USA). 1H (400 MHz) and 13C (100 MHz) NMR spectrums were measured by using Bruker Spectrospin 400.

11-bromo-1-undecanol (1 g, 3.98 mmol), sodium azide (285 mg, 4.38 mmol), and potassium iodide were dissolved in ethanol and refluxed for 20 hours. In the solution, a solvent was removed under reduced pressure, and a residue was dissolved in diethylether. The residue mixture dissolved in the ether was washed with water and dried on an anhydrous magnesium sulfate. The solvent was removed under reduced pressure. A non-purified product produced by the removal of the solvent was purified on silica gel ($R_f$=0.3, hexane:

EtOAc=5:1) through column chromatography to obtain a compound 1 (868 mg, 102.2%).

IR: 3332, 2924, 2853, 2091

$^1$H NMR (400 MHz, CDCl$_3$) δ 3.57 (t, 2H, OCH$_2$), 3.32 (s, 1H, OH), 3.25 (t, 2H, N$_3$CH$_2$), 1.57 (m, 4H, HOCH$_2$CH$_2$ (CH$_2$)$_7$CH$_2$), 1.28 (m, 14H, HOCH$_2$CH$_2$ (CH$_2$)$_7$)

$^{13}$C NMR (100 MHz, CDCl$_3$) δ62.4, 51.4, 32.6, 29.5, 29.4, 29.1, 28.8, 26.7, 25.7

Exact mass calcd for C$_{11}$H$_{23}$N$_3$O: 213.18. found: 236 [M+Na]$^+$.

The compound 1 (868 mg, 4.09 mmol), methanesulfonyl chloride (1.26 g, 11.0 mmol), and triethylamine (2.44 g, 24.1 mmol) were dissolved in THF. The reaction mixture was stirred at a room temperature for 2 hours. After addition of ice water, an organic phase in the mixture was separated from an aqueous phase in the mixture. The aqueous phase was extracted twice by diethylether. The organic phase was washed with 1 M HCl, deionized water, and saturated sodium bicarbonate. After the organic phase was dried on an anhydrous magnesium sulfate, a solvent in the organic phase was removed under reduced pressure. A resultant non-purified product was purified on silica gel (R$_f$=0.4, hexane:EtOAc=5:1) through column chromatography to obtain a compound 2 (1.17 g, 98.2%).

IR: 2925, 2854, 2092, 1180

$^1$H NMR (400 MHz, CDCl$_3$) δ 4.21 (t, 2H, OCH$_2$), 3.26 (t. CH$_2$N$_3$), 3.00 (s, 3H, CH$_3$S), 1.74 (m, 2H, OCH$_2$CH$_2$), 1.59 (m, 2H, CH$_2$CH$_2$N$_3$) 1.39-1.18 (m, 14H, OCH$_2$CH$_2$(CH$_2$)$_7$)

$^{13}$C NMR (100 MHz, CDCl$_3$) δ70.4, 51.4, 37.1, 29.4, 29.3, 29.11, 29.10, 29.0, 28.8, 26.7, 25.4

Exact mass calcd for C$_{12}$H$_{25}$N$_3$O$_3$S: 291.16. found: 314 [M+Na]$^+$.

The compound 2 (1.17 mg, 4.01 mmol) and potassium thioacetate (917 mg, 8.03 mmol) were dissolved in 90 mL of DMF. The reaction mixture was stirred at a room temperature for 1 hour. In the reaction mixture, a solvent was removed under reduced pressure, and a residue was dissolved in diethyl ether. An organic phase formed of the residue was washed with water and dried on an anhydrous magnesium sulfate. The solvent was removed under reduced pressure. A resultant non-purified product was purified on silica gel (R$_f$=0.7, hexane:EtOAc=9:1) through column chromatography to obtain a compound 3 (831 mg, 76.4%).

IR: 2924, 2853, 2092, 1690

$^1$H NMR (400 MHz, CDCl$_3$) δ 3.25 (t, 2H, CH$_2$N$_3$), 2.85 (t, 2H, SCH$_2$), 2.31 (s, 3H, CH$_3$CO), 1.57 (m, 4H, SCH$_2$CH$_2$ (CH$_2$)$_7$CH$_2$), 1.35-1.27 (m, 14H, SCH$_2$CH$_2$ (CH$_2$)$_7$)

$^{13}$C NMR (100 MHz, CDCl$_3$) δ195.8, 51.4, 30.6, 29.5, 29.4, 29.15, 29.11, 28.86, 28.81, 26.7

Exact mass calcd for C$_{13}$H$_{25}$N$_3$OS: 271.17. found: 294 [M+Na]$^+$

The compound 3 (588 mg, 2.17 mmol) was dissolved in 40 ml of methanol and 2 ml of concentrated HCl. The reaction mixture was stirred for 3 hours and quenched with water. In the reaction mixture, an aqueous phase was extracted twice by diethyl ether. In the reaction mixture, an organic phase was washed with water and dried on an anhydrous magnesium sulfate. A solvent of the organic phase was removed under reduced pressure. A resultant non-purified product was purified on silica gel (R$_f$=0.8, hexane:EtOAc=9:1) through column chromatography to obtain a compound 4 (471 mg, 94.6%).

IR: 2923, 2852, 2090

$^1$H NMR (400 MHz, CDCl$_3$) δ 3.25 (t, 2H, CH$_2$N$_3$), 2.51 (q, 2H, SCH$_2$), 1.60 (m, 4H, SCH$_2$CH$_2$ (CH$_2$)$_7$CH$_2$), 1.35-1.28 (m, 15H, HSCH$_2$CH$_2$(CH$_2$)$_7$)

$^{13}$C NMR (100 MHz, CDCl$_3$) δ51.4, 34.1, 29.5, 29.1, 29.0, 29.8, 28.4, 26.7, 24.6.

Example 5

Synthesis of 6-propagylhexylphosphorylcholine (Propagyl-Phosphorylcholine)

A solution of 1,6-hexanediol (3 g, 25.4 mmol) in DMF (20 ml) is dropwised into a suspension of sodium hydride (1.52 g, 38.1 mmol) in the DMF (20 ml) on an ice bath, and stirred for 30 minutes under the ice bath condition. Propagyl bromide (5.7 g, 38.1 mmol) in the DMF (20 ml) was added to the mixture, and then, stirred at a room temperature for 20 hours. The solvent was removed under reduced pressure. A resultant non-purified product was dissolved in diethylether. The mixture was washed with water, dried on an anhydrous magnesium sulfate, and purified on silica gel (R$_f$=0.5, hexane/EtOAc=1:1) through column chromatography to obtain a compound 5 (1.80 g, 45.4%).

IR: 3373, 3292, 2933, 2858, 1093

$^1$H NMR (400 MHz, CDCl$_3$) δ4.13(s, 2H, HCCCH$_2$O), 3.59 (t, 2H, CH$_2$OH), 3.52 (t, 2H, CH$_2$OCH$_2$), 3.03 (s, 1H, CH$_2$OH), 2.48 (s, 1H, HCCCH$_2$O), 1.58 (m, 4H, OCH$_2$CH$_2$CH$_2$CH$_2$CH$_2$), 1.38 (m, 4H, OCH$_2$CH$_2$CH$_2$CH$_2$)

$^{13}$C NMR (100 MHz, CDCl$_3$) δ 79.8, 74.3, 70.0, 62.3, 57.9, 32.5, 29.3, 25.8, 25.5

Exact mass calcd for C$_9$H$_{16}$O$_2$: 156.12. found: 179 [M+Na]$^+$

The compound 5 (600 mg, 3.84 mmol), 2-chloro-1,3,2-dioxaphosphoran2-oxide (1.09 g, 7.68 mmol), and triethylamine (777 mg, 7.68 mmol) were dissolved in 30 ml of DCM. The reaction mixture was stirred at a room temperature for 72 hours under a darkroom condition. The solvent was removed under reduced pressure. A resultant non-purified product was purified on silica gel (R$_f$=0.3, hexane/EtOAc=1:4) through column chromatography to obtain a compound 6 (700 mg, 69.5%).

The compound 6 (700 mg, 2.66 mmol) and trimethylamine (1.57 g, 26.6 mmol) were dissolved in 8 ml of acetonitrile. The reaction mixture was stirred at 60° C. for 20 hours. The solvent was removed under reduced pressure. A resultant non-purified product was purified on silica gel (chloroform:methanol is 2:1; and chloroform:methanol:water is 50:50:4; R$_f$=0.2) through column chromatography. The solvent was removed under reduced pressure. The residue was dissolved in anhydrous chloroform and filtered to obtain a compound 7(411 mg, 48.1%).

IR: 3350, 3296, 2936, 2860, 1086, 1059

$^1$H NMR (400 MHz, CD$_3$OD) δ 4.28(m, 2H, POCH$_2$CH$_2$N$^+$), 4.15 (d, 2H, HCCCH$_2$O), 3.90 (q, 2H, CH$_2$CH$_2$CH$_2$OP), 3.69 (m, 2H, POCH$_2$CH$_2$N$^+$), 3.54 (t, 2H, HCCCH$_2$OCH$_2$), 3.27 (s, 9H, N$^+$(CH$_3$)$_3$), 2.85 (t, 1H, HCCCH$_2$O), 1.64 (m, 4H, OCH$_2$CH$_2$CH$_2$CH$_2$CH$_2$), 1.44 (m, 4H, OCH$_2$CH$_2$CH$_2$CH$_2$)

$^{13}$C NMR (100 MHz, CDCl$_3$) δ79.7, 74.8, 69.6, 65.5, 59.0, 57.4, 53.5, 30.4, 29.2, 25.6, 25.3

Exact mass calcd for C$_{14}$H$_{28}$NO$_5$P: 321.17. found: 322 [M+H]$^-$).

Example 6

Surface Modification of an SPR Chip

Figure 12:
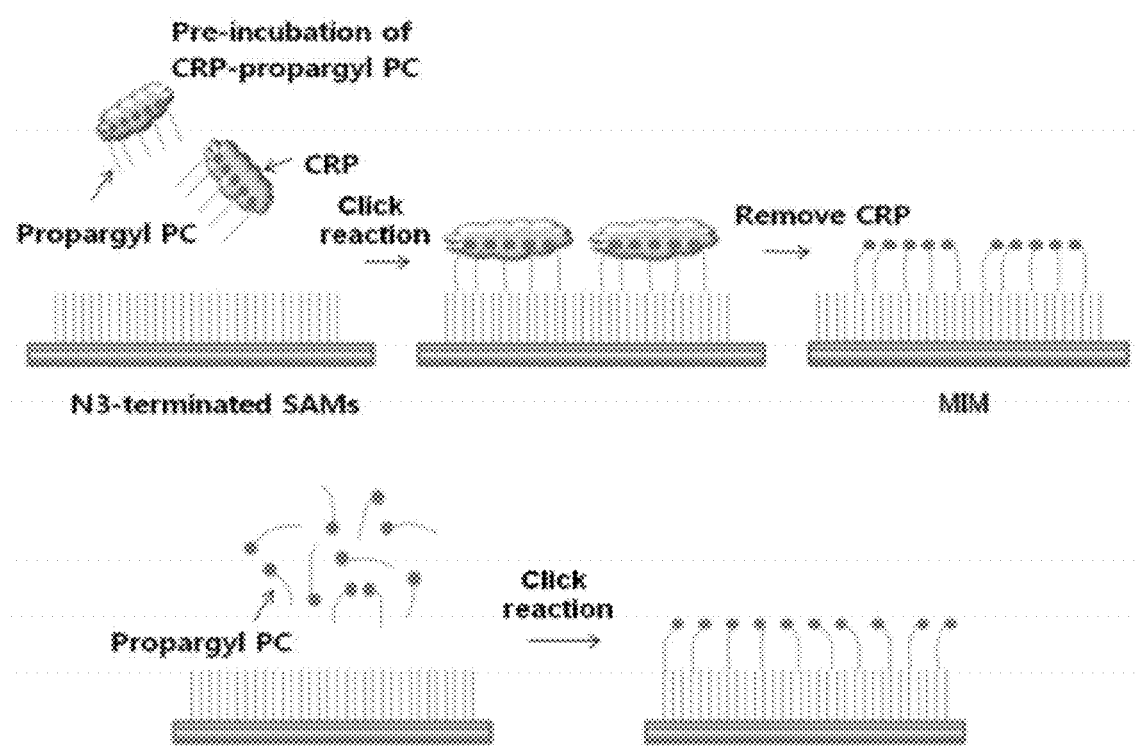
FIG. 12 is a process view showing a process for preparing a chip for detection of a C-reactive protein in an illustrative embodiment.

FIG. 12 shows a whole scheme for surface modification of an SPR chip. In order to prepare a self assembled monolayer (SAM) having an azide(N$_3$)-terminated compound, an SPR chip (15 mm×15 mm×10 mm) was immersed in 2 mM (20 ml) of an ethanol solution of 11-azidoundecane-1-thiol at a room temperature for 12 hours (FIG. 12). The substrate was thoroughly washed with ethanol several times, and then, dried under $N_2$ gas. For pre-test for a click reaction, a gold substrate (5 mm×5 mm×1 mm) was coated with 11-azidoundecane-1-thiol in the same manner as described above, and placed in a reaction mixture containing 1 μmol of propagyl-phosphorylcholine in 1 ml of PBS (FIG. 12), 0.5 μmol of copper sulfate (II)•pentahydrate, and 1 μmol of a sodium ascorbic acid at 4° C. for 16 hours.

In order to prepare a molecularly imprinted monolayer (MIM), 3.32 nmol of propagyl phosphorylcholine (PC) was pre-cultured on an ice bath for 30 minutes, with 0.66 nmol of a C-reactive protein (CRP)(molar ratio of 5:1 for propagyl phosphorylcholine: CRP) in 1 ml of a binding buffer (0.1 M Tris/HCl, 150 mM NaCl, 5 mM $CaCl_2$, pH 8.0). A 1,3-dipolar cycloaddition reaction, which is one of click chemistry reactions, was performed by placing the SPR chip coated with the self assembled monolayer of 11-azidoundecane-1-thiol in 20 ml of a PBS buffer solution containing 1.66 nmol of copper sulfate (II)•hydrate, 3.32 nmol of a sodium ascorbate, and the propagyl phosphorylcholine-CRP complex pre-cultured at 4° C. for 16 hours. The molar ratio of propagyl phosphorylcholine:copper sulfate:a sodium ascorbate was 1:0.5:1.

In order to prepare a molecularly non-imprinted monolayer, all steps were carried out as those for the molecularly imprinted monolayer, except that no CRP was added to the reaction mixture. After the reaction was finished, the surface was thoroughly washed with cool PBS and dried under $N_2$ gas.

In order to block an azide end that has not been involved in the click reaction, propagyl alcohol for another click reaction was added to the substrate. The substrate was immersed in 20 ml of PBS containing 20 μmol of propagyl alcohol, 10 μmol of copper sulfate (II)•hexahydrate, and 20 μmol of a sodium ascorbate at a room temperature for 5 hours.

In order to prepare a control polymer (CM), the SPR chip coated with the $N_3$-terminated self assembled monolayer was directly modified by propagyl alcohol through a click reaction. A surface, which was not coated with propagyl phosphorylcholine, was obtained.

In order to remove the CRP from the molecularly imprinted monolayer, the surface-modified SPR chip and the gold substrate were immersed in an elution buffer (0.1 M Tris/HCl, 10 mM EDTA, 150 mM NaCl, pH 8.0) at a room temperature for 30 minutes. Finally, the substrate was thoroughly washed with deionized water, acetone, and ethanol, and dried under $N_2$ gas.

Analysis of Surface Characteristics of an SPR Chip by Means of FT-IR

An FT-IR/ATR spectrum was acquired in a single reflection mode by using the Thermo Nicolet iS10 FT-IR spectrometer equipped with a smart aperture gazing angle (SAGA). IR spectrums of a gold surface, which has been functionalized in each of the above-described reaction steps, were obtained in a range of 650 $cm^{-1}$-4000 $cm^{-1}$. All the spectra were equalized through 512 scan and reported in a penetration mode to a clean gold surface.

Analysis of CRP Binding through a surface Plasmon Resonance (SPR) Research

CRP binding to each substrate was measured by SPR LAB (the K-MAC company). Dilution and elution of the sample were carried out with a flow rate of 20 ml/min at 25° C. by means of a binding buffer. Binding of the CRP onto the SPR chip was carried out by one dose of injection of 300 of the protein solution of 100 pM to 400 nM in the binding buffer. A N-serum was diluted to be a 2% solution in a binding buffer. BSA was prepared to be a 1% solution in PBS. In the binding buffer, 10 mM of free phosphocholine (f-phosphocholine) was used to identify phosphorylcholine specific binding of the CRP. The protein binding was recorded with a resonance angle and reported with incidence angle shift (Δ°).

Analysis of Surface Characteristics of an SPR Sensor

Figure 13:
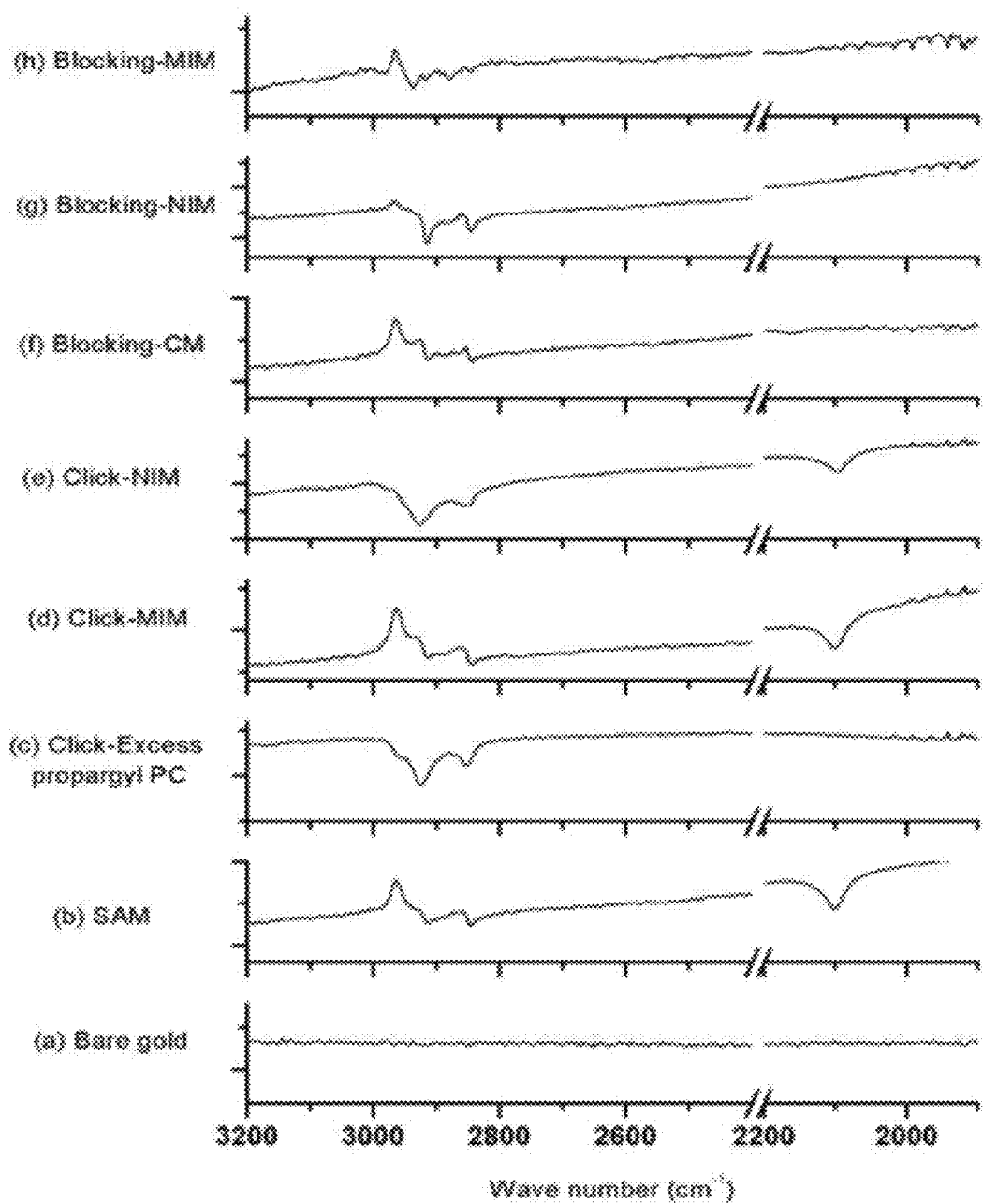
FIG. 13 shows FT-IR spectrums for surface modification according to an example.

In order to introduce an azide group onto a surface of the gold substrate for continuous click chemistry, the gold substrate was immersed in 2 mM of an ethanol solution of 11-azidoundecane-1-thiol, which was azide-containing thiol, at a room temperature for 12 hours. Characteristics of a self assembled monolayer obtained from the immersion were analyzed by means of FT-IR/ATS. In the IR spectrums, characteristic peaks of the self assembled monolayer were observed at 2850 $cm^{-1}$ (symmetric methyl C—H stretching), 2930 $cm^{-1}$ (non-symmetric methyl C—H stretching), and 2090 $cm^{-1}$ (non-symmetric $N_3$ stretching mode) (FIG. 13b).

In order to identify that the click chemistry is caused by propagyl phosphorylcholine, an excess molar concentration of propagyl phosphorylcholine (1 mM) was added to the reaction mixture containing the gold substrate coated with 11-azidoundecane-1-thiol. FIG. 13c shows an IR spectrum of the gold substrate, in which propagyl phosphorylcholine at a 4-site of triazole was substituted with an excess amount of propagyl phosphorylcholine. In the spectrum, the non-symmetric $N_3$ stretching peak has disappeared at 2090 $cm^{-1}$. This shows that mounting of propagyl phosphorylcholine onto the surface was accomplished by successful coupling between an azide group and an acetylene group.

In synthesis of a molecularly non-imprinted monolayer (Click-NIM) and a molecularly imprinted monolayer (Click-MIM), a molar concentration of propagyl phosphorylcholine was 166 nM. In the IR spectrum, the non-symmetric $N_3$ stretching peak has not disappeared at 2090 $cm^{-1}$ (FIG. 13d and FIG. 13e). This shows that the free $N_3$ group remains on the surface.

In order to quench an activity surface of the free $N_3$ group, propagyl alcohol, which is another agent for blocking click reaction, is added. After the blocking reaction, IR spectrums (FIGS. 13f, 13g, and 13h) for the control polymer (Blocking-CM), the molecularly non-imprinted monolayer (Blocking-NIMM), and the molecularly imprinted monolayer (Blocking-MIM) show that the $N_3$ group is completely protected by propagyl alcohol. It is identified that the non-symmetric $N_3$ stretching peak has disappeared completely at 2090 $CM^{-1}$. The peaks at 2850 $CM^{-1}$ (symmetric methyl C—H stretching) and 2930 $CM^{-1}$ (non-symmetric methyl C—H stretching) were preserved even after the click reaction.

Analysis of Binding Characteristics of a CRP to a Molecularly Imprinted Monolayer The SPR technology relates to an optical method to measure a refractive index of a very thin layer of a material absorbed to a metal. Degree of binding between a target molecule in a solution and a molecular receptor fixed onto the chip surface was easily observed and quantified by monitoring reflectivity variation. One of advantages of the SPR technology relates to exhibiting high sensitivity to the target molecule or the receptor molecule without using labeling. The SPR was used to research binding of the CRP onto the modified gold surface.

In the system used in an illustrative embodiment, i.e., SPR LAB (the K-MAC company), reflectivity was measured with a function for an incidence angle of a light beam. Angle variation, to a coated gold sensor surface, was measured with about 1 milli degree of resolution corresponding to ~10 $pg/mm^2$ of a protein bound onto the coated surface. Analysis for the SPR system was measured by variation of a resonance angle, which was related to an amount of an analyte bound onto the sensor surface. A difference in a normal-state SPR signal is defined by incidence angle shift (Δ°) and proportional to a mass of an absorbed protein (0.1°≈1 ng/mm²). The incidence angle shift was calculated by an incidence angle after washing with a buffer for 5 minutes and an incidence angle prior to injection of a protein.

Through an X-ray crystallography research, it was identified that a diameter of the CRP was 12 nm, and a binding region of the SPR chip was 28.9 mm. Accordingly, based on 115 kDa of the molecular weight of the CRP, the whole binding ability of the SPR chip calculated to 49 ng (=1.7 ng/mm²).

Figure 14:
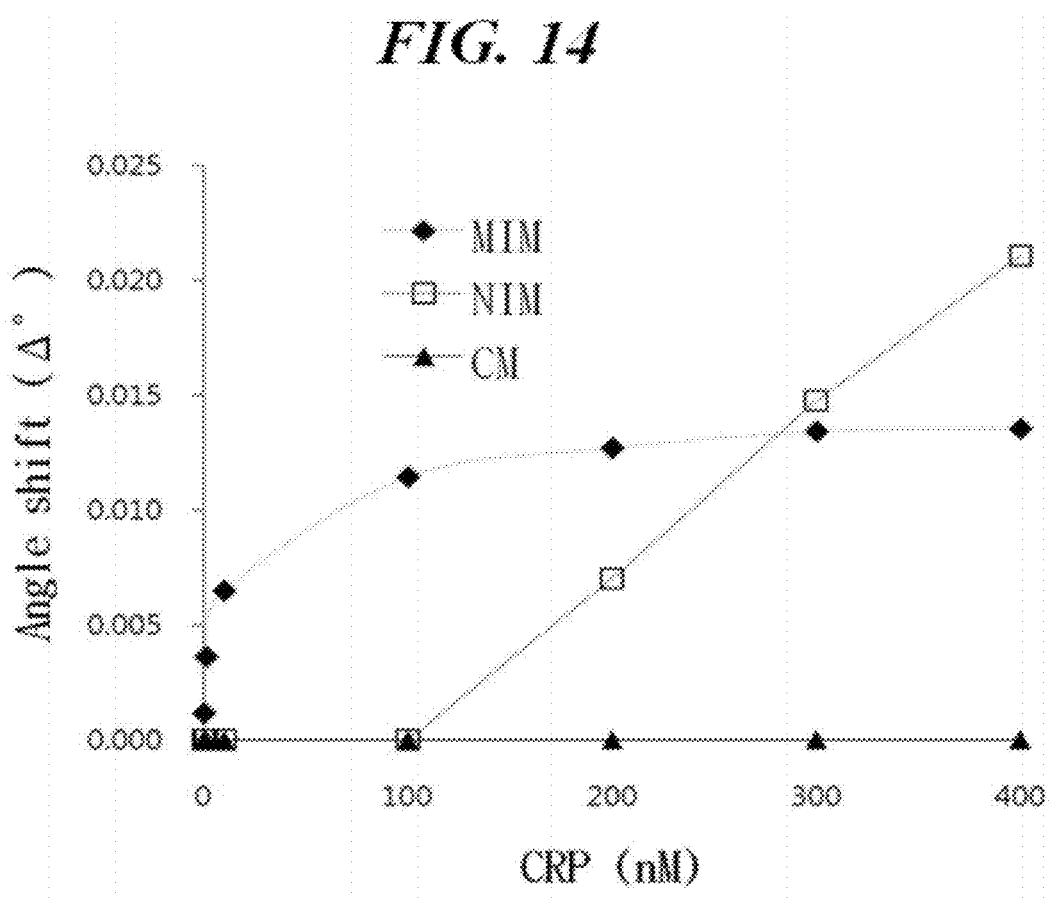
FIG. 14 is a graph showing concentration-dependent binding of a C-reactive protein (CRP) to each of a control polymer (CM), and a molecularly non-imprinted monolayer, and a molecularly imprinted monolayer (examples)

FIG. 14 shows an SPR signal by binding of a C-reactive protein (CRP) to a gold substrate, a control polymer (CM), a molecularly non-imprinted monolayer (NIM), and a molecularly imprinted monolayer (MIM), respectively. In case of the control polymer, no CRP binding was observed. In case of the molecularly imprinted monolayer (MIM) with 10 nM of the CRP concentration, binding of the CRP was almost half in comparison with that in the saturated state. Binding in case of 100 nM of the CRP concentration is almost same with that in the saturated state. In case of the molecularly non-imprinted monolayer (NIM), no CRP binding was observed up to 100 nM of the CRP concentration. CRP binding rapidly increases from 200 nM to 400 nM. The concentration-dependent binding of the CRP to each of the molecularly non-imprinted monolayer and the molecularly imprinted monolayer shows that phosphorylcholine has been successfully introduced onto the gold surface through click chemistry, and provides a binding ability of the CRP to each of the molecularly non-imprinted monolayer and the molecularly imprinted monolayer. If there is no non-specific binding in binding between the molecularly non-imprinted monolayer and the CRP, it is likely that a total CRP binding ability (the number of binding sites) in the molecularly non-imprinted monolayer is greater than that in the molecularly imprinted monolayer.

A binding constant and a maximum binding ability ($R_{max}$) between the CRP and each of the molecularly non-imprinted monolayer and the molecularly imprinted monolayer were calculated by using a Langmuir absorption model. The correlation between CRP concentration and angle shift as shown FIG. 14 is expressed with a following reaction formula, i.e., a modified Langmuir equation model:

$$\frac{C}{R} = \frac{C}{R_{max}} + \frac{1}{R_{max} \cdot K_A} \quad (1)$$

Here, R is incidence angle shift caused by CRP binding in an equilibriuma state, C is CRP concentration, $R_{max}$ is angle shift when C is infinite, and $K_A$ is an apparent binding constant.

Figure 15:
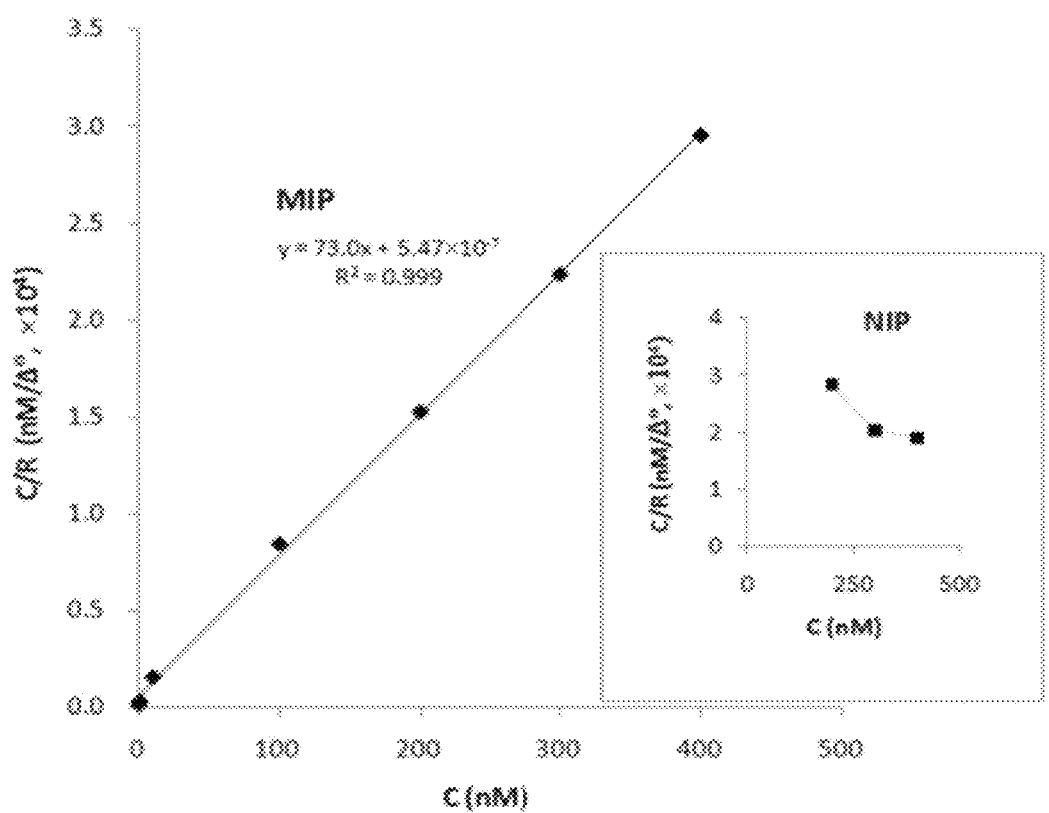
FIG. 15 is a graph for plotting binding of a C-reactive protein to each of a molecularly non-imprinted monolayer and a molecularly imprinted monolayer according to the Langmuir isotherm equation.

As a result of plotting according to the above equation (1), a graph in a straight line was obtained, and a proportion of slope to the intercept was $K_A$ (FIG. 15). A $K_A$ value for the molecularly imprinted monolayer and the CRP was determined to be $1.33 \times 10^8$ $M^{-1}$. However, binding between the molecularly non-imprinted monolayer and the CRP was not plotted by the Langmuir equation, and C and C/R are in the in inverse proportion to each other. Although an exact cause for the relation of inverse proportion is not provided herein, it is assumed that the relation of inverse proportion can be explained in non-specific binding of the CRP to the molecularly non-imprinted monolayer.

Upon calculation, a maximum coverage of the CRP on the SPR chip was 49 ng. However, when 100 nM of the CRP was injected into a sample tube (buffer volume of 100 nM=12.0 ng/ml and chip surface=51.5 ml), total 618 ng of the CRP was injected onto the chip surface during driving of the sample. Since CRP binding to the NIM started in concentration between 100 nM and 200 nM of the CRP, the surface can be covered completely by the CRP at an initial stage of the CRP binding. Thereafter, protein-protein attraction causes sudden non-specific binding of the CRP to the NIM in addition to PC-specific absorption.

With the proviso that 1 ng≈Δ0.1°, $R_{max}$ of the MIM is 0.014°, which corresponds to 4 ng/mm² of the CRP binding and 8% of a calculated maximum coverage of the SPR chip surface.

Effect of Free Phosphocholine

Figure 16:
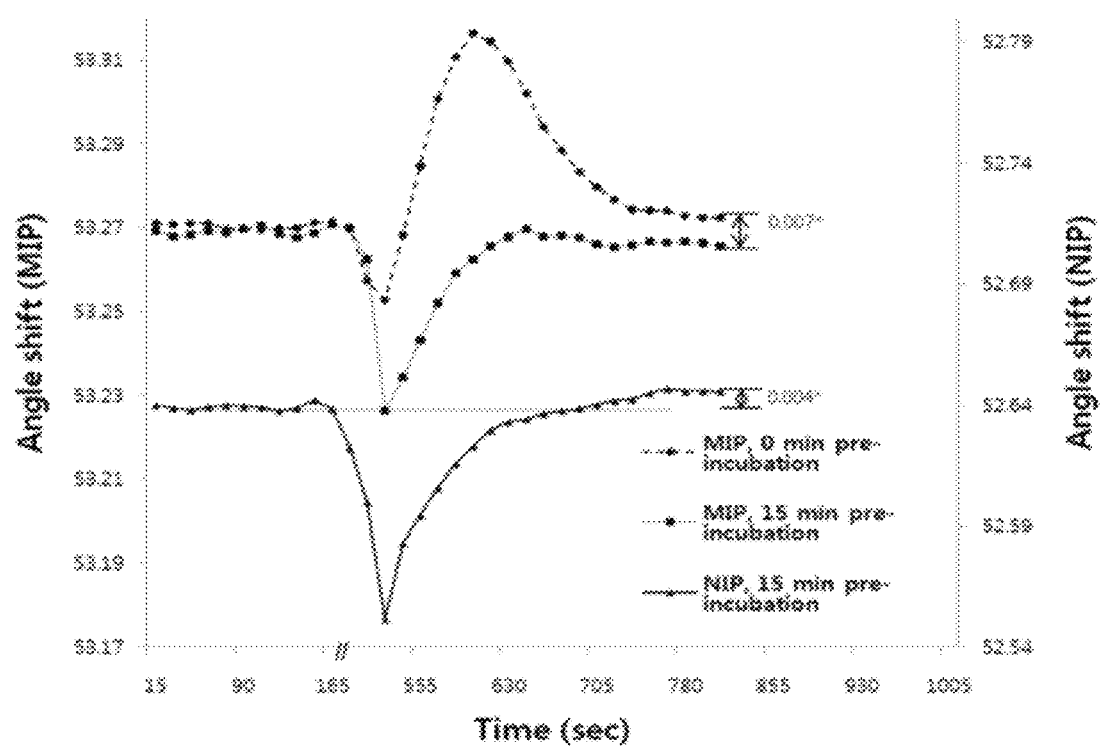
FIG. 16 is a graph showing an effect of free phosphocholine in binding of a C-reactive protein to each of a molecularly non-imprinted monolayer and a molecularly imprinted monolayer (examples)

In order to study whether specific binding of a CRP to a molecular receptor occurs, an effect of free phosphocholine (fPC) had been researched. For the molecularly imprinted monolayer, two sets of 300 μl of a binding buffer sample containing 200 nM of the CRP and 10 mM of the fPC were prepared. One sample was directly injected without undergoing pre-culture. The other sample was injected after undergoing pre-culture at a room temperature for 15 minutes. FIG. 16 shows results for an effect of fPC in CRP binding to the molecularly imprinted monolayer and the molecularly non-imprinted monolayer. In the injection of the sample, the rapid decrease of the incidence angle was merely a result of an effect of the fPC (data therefor are not illustrated) by deprivation of calcium ions from the surface in the form of a calcium-fPC ionic compound. If there is no pre-culturing of the CRP and the fPC, the incidence angle shift) (0.007° was observed in the molecularly imprinted monolayer. An amount of CRP binding corresponded to injection of 8.2 nM of the CRP according to a standard curve (FIG. 14, y=0.0016ln(x)+0.0368) for a binding ability of the molecularly imprinted monolayer, and was almost half of $R_{max}$ (0.014) of the molecularly imprinted monolayer. In the case where the sample has been pre-cultured, no binding was observed on the molecularly imprinted monolayer. This means that the fPC formed a complex with the CRP during the pre-culturing of the sample. The fPC-CRP complex cannot be bound to the molecular receptor on the molecularly imprinted monolayer. However, if there is no pre-culturing of fPC-CRP, the CRP can be partially bound to a PC receptor site. This shows that CRP binding to the molecularly imprinted monolayer is very specific to the molecular receptor synthesized through molecularly imprinting and click chemistry. When a CRP-fPC solution that had been pre-cultured for 15 minutes was injected into the molecularly non-imprinted monolayer, the binding was observed with 0.004° of angle shift. The result was partially due to that the CRP binding to the molecularly non-imprinted monolayer according to the relation shown in FIG. 14 is non-specific binding. This is probably because when the binding site of the CRP to phosphorylcholine is blocked by the fPC in the sample, absorption onto the surface of the molecularly non-imprinted monolayer occurs.

In the molecularly non-imprinted monolayer, considering results of the Langmuir isotherm research presented in FIG. 15, which is not applied to the Langmuir isotherm model, it is believed that binding of the CRP to the molecularly non-imprinted monolayer involved not only the phosphorylcholine receptor-adjusted specific binding but also non-specific binding which is not bound via the phosphorylcholine receptor.

Selectivity of the SPR Chip

Figure 17:
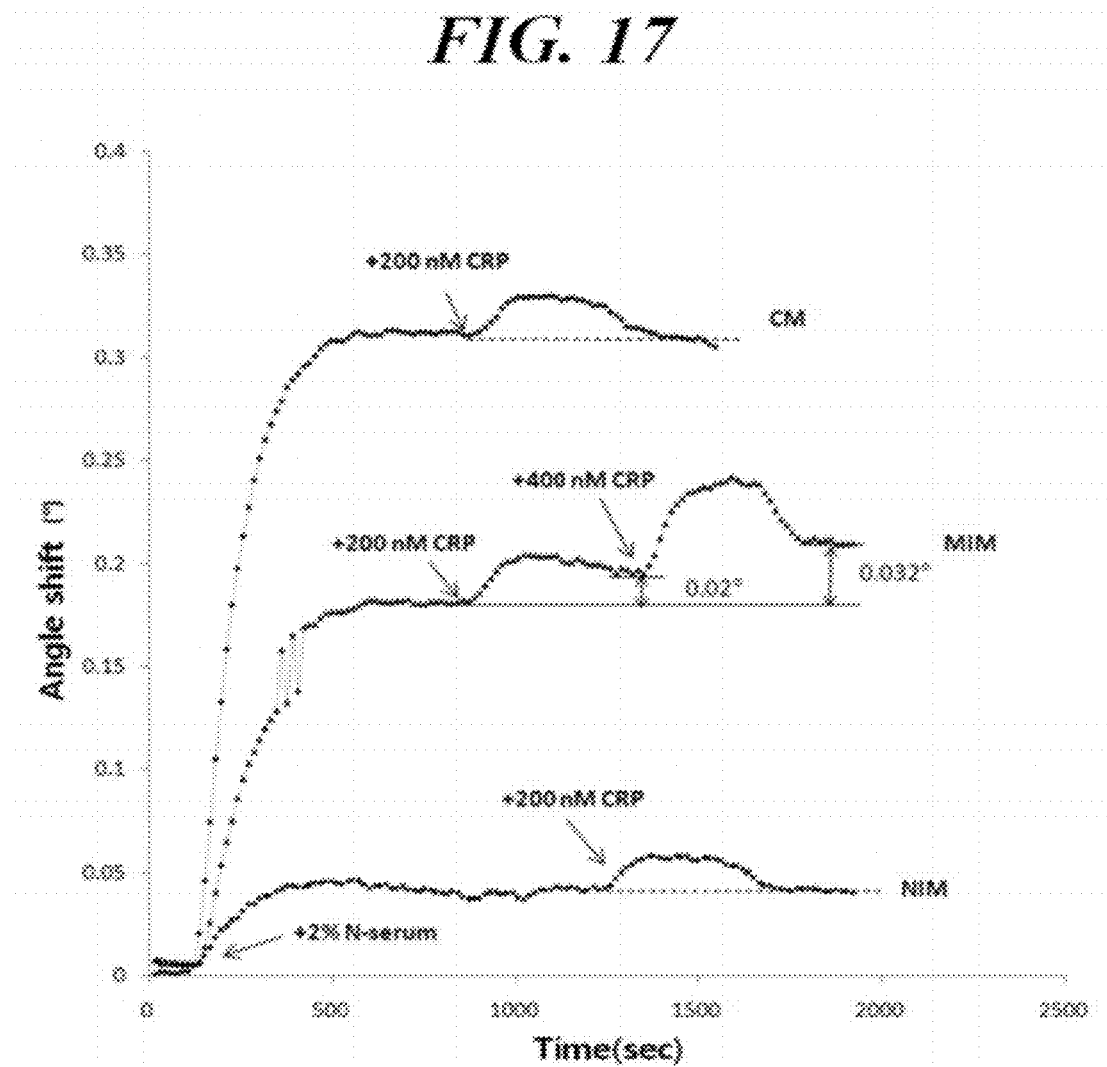
FIG. 17 is a graph showing binding of a C-reactive protein in serums to each of a control polymer, a molecularly non-imprinted monolayer, and a molecularly imprinted monolayer (examples)
Figure 18:
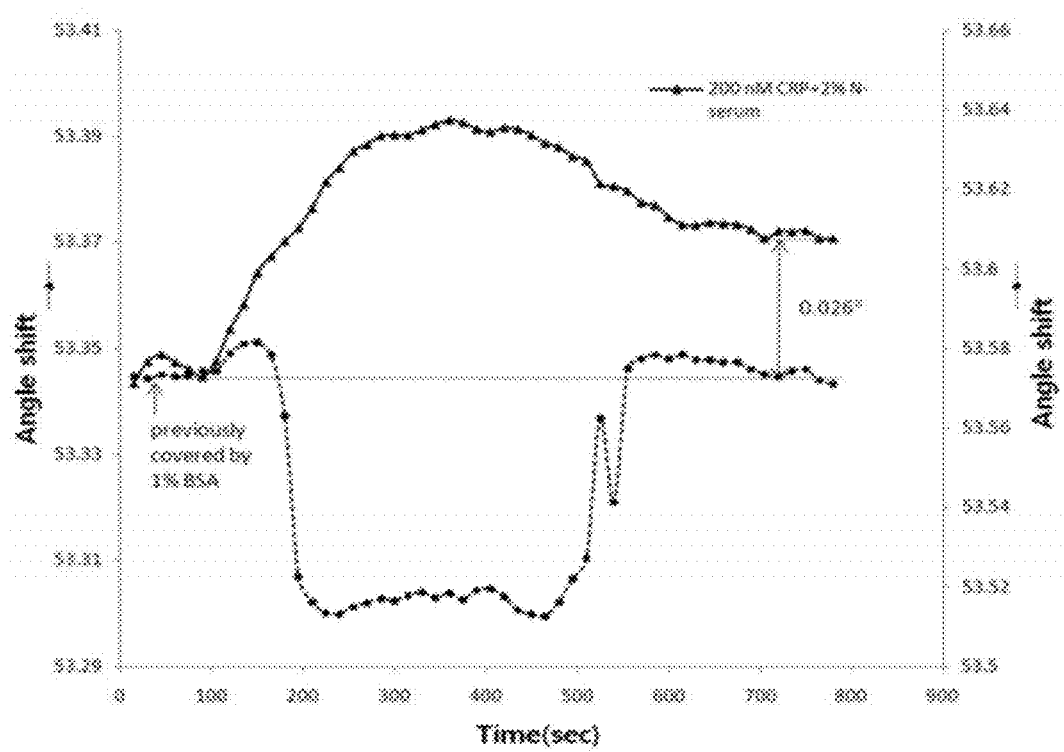
FIG. 18 is a graph showing an effect of free phosphocholine in binding of a C-reactive protein in a complex matrix in an example.

Binding selectivity of a molecular receptor (molecularly imprinted structure) synthesized in an illustrative embodiment has been researched. A 2% N-serum is injected. After the surface is stabilized, 200 nM of a CRP is injected. In the binding of the CRP to the CM and the molecularly non-imprinted monolayer, the binding of the CRP was not occurred after the 2% N-serum covers the surface. However, in the molecularly imprinted monolayer, incidence angle shift by 200 nM (0.020°) and 400 nM (0.032°) of the CRP was observed even after the 2% N-serum covers the surface (FIG. 17). This means that the molecular receptor on the molecularly imprinted monolayer surface was not substituted with other serum proteins. In FIG. 14, a concentration-dependent CRP binding curve shows that incidence angle shift is 0.013 in case of 200 nM of the CRP and 0.014 in case of 400 nM of the CRP. The difference in angle shift resulted from the following different measurement conditions: (1) the 2% N-serum improved stability of the binding state of the CRP to the molecular receptor through protein-protein interaction, and reduced removal of the bound CRP from the surface through washing; (2) instrumental deviation caused by injection of a large amount of protein, which corresponds to ~420 μg of a serum protein in 300 μl of the 2% N-serum (based on 70 mg/ml of original serum protein concentration). In order to identify phosphorylcholine-specific binding of the CRP to the SPR chip under the presence of an N-serum protein, 10 mM of the fPC was treated in the sample solution (2% N-serum+200 nM of the CRP) and pre-cultured for 15 minutes. Prior to injection of the sample, 1% BSA was injected on the surface for protection from non-specific binding by a large amount of proteins in the serum. FIG. 18 shows that even if serum proteins are simultaneously treated in the molecular receptor, the fPC completely inhibited the CRP binding to the molecularly imprinted monolayer. This means that the incidence angle shift by the CRP and the N-serum mixture, as observed in the molecularly imprinted monolayer, was caused from the CRP-receptor binding, and not non-specific binding of other proteins. When the 2% serum and 200 nM of the CRP were simultaneously treated, 0.026° of angle shift was observed (FIG. 18). As a result, the CRP in serum proteins was specifically bound to the receptor and thus can be applied to detection of CRPs in a human serum.

INDUSTRIAL APPLICABILITY

As described, the present disclosure relates to a method for preparing a molecularly imprinted structure, providing an improved effect in detection of pentraxin proteins such as a C-reactive protein, a serum amyloid P component, and PTX-3. The present disclosure may be applied to various types of molecularly imprinted polymers, using a complex of a reactive group-pentraxin protein ligand capable of polymerizing a pentraxin protein and a reactive ligand directly on a reactive surface. Also, it is possible to prepare a film and a bead for detection of a pentraxin protein by using the method. Accordingly, it is possible to more easily detect and purify a pentraxin protein by using a complex of a molecularly imprinted reactive group-pentraxin protein ligand having a stronger binding force than that of a ligand of a single pentraxin protein.

What is claimed is:

1. A method for preparing a molecularly imprinted structure for detection of a pentraxin protein, the method comprising:

binding the pentraxin protein and a reactive ligand having a following structural formula to form a complex;

chemically reacting the complex of the pentraxin protein and the reactive ligand on a reactive surface of a support; and removing the pentraxin protein from the reacting material by washing the reacting material with an elution buffer solution L—S—R                    [Structural Formula]

L: ligand for binding with the pentraxin protein
R: reactive group
S: linker for linking between the ligand for binding with the pentraxin protein and the reactive group.

2. The method for preparing a molecularly imprinted structure for detection of a pentraxin protein claimed in claim 1, wherein the pentraxin protein includes one selected from the group consisting of a C-reactive protein, a serum amyloid P component, and PTX-3(Pentraxin 3).

3. The method for preparing a molecularly imprinted structure for detection of a pentraxin protein claimed in claim 2, wherein the ligand (L) of the pentraxin protein is phosphocholine with the proviso that the pentraxin protein is the C-reactive protein, the ligand (L) of the pentraxin protein is proline with the proviso that the pentraxin protein is the serum amyloid P component, and the ligand (L) of the pentraxin protein includes C1q with the proviso that the pentraxin protein is PTX-3.

4. The method for preparing a molecularly imprinted structure for detection of a pentraxin protein claimed in claim 1, wherein the reactive group (R) includes a polymerizable group, or a functional group reacting with metal or a metal oxide.

5. The method for preparing a molecularly imprinted structure for detection of a pentraxin protein claimed in claim 4, wherein the polymerizable group includes a radical polymerization monomer selected from vinyl, styryl, acryloyl methacryloyl, sorbyl, and dienoyl, and the functional group reacting with a metal or a metal oxide a metal reactive group selected from thiol, disulfide, and thioether, or a metal oxide reactive group selected from trichlorosilyl, trimethylsilyl triisopropylsilyl, and catechol.

6. The method for preparing a molecularly imprinted structure for detection of a pentraxin protein claimed in claim 1, wherein the linker (S) includes alkyl, aryl, arylalkyl, an oligoethylene oxide, or a combination thereof.

7. The method for preparing a molecularly imprinted structure for detection of a pentraxin protein claimed in claim 1, wherein the reactive surface is a surface of a film, nanoparticles, a nano-wire, or porous particles.

8. The method for preparing a molecularly imprinted structure for detection of a pentraxin protein claimed in claim 1, wherein the chemically reacting is a polymerization reaction of a monomer and a crosslink agent with the reactive group of the reactive ligand, or a chemical binding reaction of a metal or a metal oxide with the reactive group of the reactive ligand.

9. The method for preparing a molecularly imprinted structure for detection of a pentraxin protein claimed in claim 8, wherein the polymerization reaction is a thermal polymerization or a photo-polymerization reaction by a radical polymerization initiator or a photo-polymerization initiator.

10. The method for preparing a molecularly imprinted structure for detection of a pentraxin protein claimed in claim 1,
 wherein the pentraxin protein includes a C-reactive protein, and the method further comprises:
 (a) preparing a styrene-phosphocholine ligand, in which styrene and a phosphocholine ligand are bound to each other;
 (b) reacting the styrene-phosphocholine ligand with a C-reactive protein;
 (c) adding the reacting material to a buffer solution containing a monomer, a crosslink agent, and an initiator and mixing them;
 (d) performing a UV photopolymerization reaction for the mixture to obtain a polystyrene polymer to which the C-reactive protein is bound; and
 (e) removing the C-reactive protein by washing the polystyrene polymer with an elution buffer solution.

* * * * *

UNITED STATES PATENT AND TRADEMARK OFFICE
CERTIFICATE OF CORRECTION

PATENT NO. : 9,034,258 B2  
APPLICATION NO. : 13/297556  
DATED : May 19, 2015  
INVENTOR(S) : Sang Won Jeong et al.

Page 1 of 1

It is certified that error appears in the above-identified patent and that said Letters Patent is hereby corrected as shown below:

In the Specification,

Column 16, line 59; replace "$[M+H]^-$)." with -- "$[M+H]^+$). --

Column 20, line 34; replace "(0.007°°" with -- (0.007°) --

In the Claims,

Column 22, line 39; insert -- itaconoyl -- between "methacryloyl" and "sorbyl"

Signed and Sealed this  
Fifth Day of January, 2016

Michelle K. Lee  
*Director of the United States Patent and Trademark Office*